US010925519B2

(12) United States Patent
Branch et al.

(10) Patent No.: US 10,925,519 B2
(45) Date of Patent: *Feb. 23, 2021

(54) ROBOTIC KNEE TESTING (RKT) DEVICE HAVING DECOUPLED DRIVE CAPABILITY AND SYSTEMS AND METHODS PROVIDING THE SAME

(71) Applicant: ERMI, Inc., Atlanta, GA (US)

(72) Inventors: Thomas P. Branch, Atlanta, GA (US); Shaun Kevin Stinton, Chamblee, GA (US); Thomas Christopher Madden, Atlanta, GA (US); Edward Dittmar, Marietta, GA (US); Nathaniel K. DeJarnette, Lilburn, GA (US); Timothy Shary, Atlanta, GA (US)

(73) Assignee: RoboDiagnostics LLC, Atlanta, GA (US)

( * ) Notice: Subject to any disclaimer, the term of this patent is extended or adjusted under 35 U.S.C. 154(b) by 485 days.

This patent is subject to a terminal disclaimer.

(21) Appl. No.: 15/812,500

(22) Filed: Nov. 14, 2017

(65) Prior Publication Data
US 2018/0146891 A1 May 31, 2018

Related U.S. Application Data

(63) Continuation of application No. 14/029,780, filed on Sep. 17, 2013, now Pat. No. 9,814,411.
(Continued)

(51) Int. Cl.
*A61H 1/02* (2006.01)
*A61B 5/11* (2006.01)
*A61B 5/00* (2006.01)

(52) U.S. Cl.
CPC .......... *A61B 5/1121* (2013.01); *A61B 5/4585* (2013.01); *A61B 5/702* (2013.01);
(Continued)

(58) Field of Classification Search
CPC ............ A61G 13/0036; A61G 13/0045; A61G 13/0063; A61G 13/0072; A61G 13/0081;
(Continued)

(56) References Cited

U.S. PATENT DOCUMENTS

| T100,602 I4 | 5/1981 | Roley et al. |
|---|---|---|
| 4,294,141 A | 10/1981 | Miller |

(Continued)

FOREIGN PATENT DOCUMENTS

| CA | 2615171 | 1/2007 |
|---|---|---|
| DE | 3609535 | 9/1987 |

(Continued)

OTHER PUBLICATIONS

Amendments Under Article 34 and Response to First Written Opinion on Preliminary Examination in International Application No. PCT/US13/60229, dated Jul. 17, 2014, 40 pages.
(Continued)

*Primary Examiner* — Michael J Tsai
(74) *Attorney, Agent, or Firm* — Lempia Summerfield Katz LLC

(57) ABSTRACT

Various limb manipulation and evaluation devices are provided. The devices generally include three drives, namely a first drive configured to manipulate a first bone relative to a second bone in a first direction, a second drive configured to manipulate the first bone relative to the second bone in a second direction, a third drive configured to manipulate the first bone relative to the second bone in a second direction. The three directions are different relative to each other and in some embodiments represent three distinct axes. The devices are further configured such that at least one of the drives is mutually decoupled relative to at least one other drive, such that operation of the one drive does not affect the position or movement of the another drive. One or multiple
(Continued)

of the drives may be decoupled. A corresponding method of operating such decoupled drives is also provided.

20 Claims, 24 Drawing Sheets

Related U.S. Application Data

(60) Provisional application No. 61/702,105, filed on Sep. 17, 2012.

(52) U.S. Cl.
CPC ... *A61H 1/0237* (2013.01); *A61H 2201/1215* (2013.01); *A61H 2203/0456* (2013.01); *A61H 2205/106* (2013.01)

(58) Field of Classification Search
CPC .............. A61G 13/123; A61G 13/1235; A61G 13/124; A61G 13/125; A61G 13/1255; A61H 1/00; A61H 1/02; A61H 2001/0203; A61H 2001/0207; A61H 1/0274; A61H 1/0277; A61H 1/0281; A61H 1/0237; A61H 1/024; A61H 1/001; A61H 1/003; A61H 1/005
See application file for complete search history.

(56) References Cited

U.S. PATENT DOCUMENTS

| | | | |
|---|---|---|---|
| 4,407,277 A | 10/1983 | Ellison | |
| 4,586,495 A | 5/1986 | Petrofsky | |
| 4,650,183 A | 3/1987 | McIntyre | |
| 4,727,860 A | 3/1988 | McIntyre | |
| 4,733,859 A | 3/1988 | Kock et al. | |
| 4,771,548 A | 9/1988 | Donnery | |
| 4,782,831 A | 11/1988 | Gallant | |
| 4,823,807 A | 4/1989 | Russell et al. | |
| 4,825,852 A | 5/1989 | Genovese et al. | |
| 4,834,073 A | 5/1989 | Bledsoe et al. | |
| 4,909,262 A | 3/1990 | Halpern et al. | |
| 4,930,497 A | 6/1990 | Saringer | |
| 5,027,799 A | 7/1991 | Laico et al. | |
| 5,056,535 A | 10/1991 | Bonnell | |
| 5,148,800 A * | 9/1992 | Pecheux | A61H 1/0237 482/79 |
| 5,211,161 A | 5/1993 | Stef | |
| 5,228,432 A | 7/1993 | Kaiser et al. | |
| 5,335,674 A | 8/1994 | Siegler | |
| 5,382,225 A | 1/1995 | Sutcliffe | |
| 5,399,147 A | 3/1995 | Kaiser | |
| 5,402,800 A | 4/1995 | Hollis | |
| 5,435,321 A | 7/1995 | McMillen et al. | |
| 5,645,079 A | 7/1997 | Zahiri et al. | |
| 6,599,255 B2 | 7/2003 | Zhang | |
| 6,669,660 B2 | 12/2003 | Branch | |
| 6,821,231 B1 | 11/2004 | Hall | |
| 6,872,186 B2 | 3/2005 | Branch et al. | |
| 7,041,069 B2 | 5/2006 | West | |
| 7,479,121 B2 | 1/2009 | Branch | |
| 7,547,289 B2 | 6/2009 | Branch | |
| 7,559,766 B2 | 7/2009 | Epley et al. | |
| 7,628,766 B1 | 12/2009 | Kazerooni et al. | |
| 7,665,167 B2 | 2/2010 | Branch et al. | |
| 7,753,862 B2 | 7/2010 | Branch et al. | |
| 7,854,685 B2 | 12/2010 | Cole et al. | |
| 7,951,097 B2 | 5/2011 | Schaeffer | |
| 7,985,227 B2 | 7/2011 | Branch et al. | |
| 2004/0003468 A1* | 1/2004 | Mitsuishi | A61H 1/0237 5/624 |
| 2004/0260208 A1 | 12/2004 | Laprade et al. | |
| 2005/0222573 A1 | 10/2005 | Branch et al. | |
| 2006/0064048 A1 | 3/2006 | Stano | |
| 2006/0097557 A1 | 5/2006 | Tholkes et al. | |
| 2007/0055176 A1 | 3/2007 | Branch et al. | |
| 2007/0123997 A1 | 5/2007 | Herr et al. | |
| 2009/0124936 A1 | 5/2009 | Branch et al. | |
| 2009/0264797 A1* | 10/2009 | Mayr | A61B 5/1071 600/595 |
| 2010/0179605 A1 | 7/2010 | Branch et al. | |
| 2010/0313897 A1* | 12/2010 | Schaeffer | A61H 1/0222 128/845 |
| 2012/0046540 A1 | 2/2012 | Branch et al. | |
| 2012/0085353 A1* | 4/2012 | Siston | A61B 90/06 128/845 |
| 2013/0060171 A1 | 3/2013 | Fu et al. | |

FOREIGN PATENT DOCUMENTS

| | | |
|---|---|---|
| DE | 3925014 | 1/1991 |
| EP | 0204639 | 12/1986 |
| EP | 0293372 | 6/1991 |
| EP | 1219240 | 7/2002 |
| WO | 8804536 | 6/1988 |
| WO | 9302621 | 2/1993 |
| WO | 02096274 | 12/2002 |
| WO | 2007009063 | 1/2007 |
| WO | 2009064367 | 5/2009 |
| WO | 2012021726 | 2/2012 |

OTHER PUBLICATIONS

B.D. Beynnon et al., "The Effect of Functional Knee-Braces on Strain on the Anterior Cruciate Ligament in Vivo", Journal of Bone and Joint Surgery, Oct. 1992, pp. 1298-1312, vol. 74A, No. 9.
Benjamin S. Un et al., "A New Device to Measure Knee Laxity During Weightbearing and Non-Weightbearing Conditions", Journal of Orthopaedic Research, Aug. 15, 2000, pp. 1185-1191, vol. 19, No. 6.
Dale M. Daniel, M.D., "Reference, Maintenance & Users Guide for the Knee Ligament Arthrometer, MEDmetric Knee Ligament Arthrometer, Models KT1000 and KT2000", MEDmetric Corporation, First Edition, May 1993, 51 pages.
International Preliminary Report on Patentability in International Application No. PCT/USI3/60229, dated Jan. 29, 2015, 46 pages.
International Search Report and Written Opinion in International Application No. PCT/US2013/060229, dated Dec. 5, 2013, 12 pages.
Keith J. Markolf et al., "In Vivo Knee Stability: A Quantitative Assessment Using an Instrumented Clinical Testing Apparatus", Journal of Bone and Joint Surgery, American Vol., Jul. 1978, pp. 664-674, vol. 60, No. 5.
Konsei Shino et al., "Measurement of Anterior Instability of the Knee: A New Apparatus for Clinical Testing", Journal of Bone and Joint Surgery, British Vol., Aug. 1987, pp. 608-613, vol. 69, No. 4.
Li-Qun Zhang et al., "Dynamic and Static Properties of the Human Knee Joint in Axial Rotation", Proceedings of the 19th Annual International Conference of the IEEE, Oct. 30, 1997, pp. 1738-1741, vol. 4.
M. Van Der Esch et al., "Reproducibility of Instrumented Knee Joint Laxity Measurement in Healthy Subjects", Rheumatology (Oxford, England), May 2006, pp. 595-599, vol. 45, No. 5.
Medmetric Corporation, "In These Times of Managed Care, Measured Outcomes are Crucial?", 1 page, http://web.archive.org/web/20040610111553/http://medmetric.com.
MEDmetric Corporation/KT1000/S?, 2 pages, http://web.archive.org/web/20040628060104/www.kt1000.com/kts.html.
MEDmetric Corporation/KT2000?, 2 pages, http://web.archive.org/web/20040618192953/www.kt1000.com/kt2.htm.
PCT Demand Under Article 31 of the Patent Cooperation Treaty in International Application No. PCT/US13/60229, filed Jul. 17, 2014, 10 pages.
Sandra Schultz et al., "Measurement of Varus-Valgus and Internal-External Rotational Knee Laxitites In Vivo—Part I: Assessment of Measurement Reliability and Bilateral Asymmetry", Journal of Orthopaedic Research, Aug. 2007, pp. 981-988, vol. 25, No. 8.

(56) References Cited

OTHER PUBLICATIONS

Stephen C. Shoemaker et al., "In Vivo Rotatory Knee Stability: Ligamentous and Muscular Contributions", Journal of Bone and Joint Surgery, 1982, pp. 208-216, vol. 64, No. 2.

Thomas P. Branch, M.D., "Instrumented Examination of Anterior Cruciate Ligament Injuries: Minimizing Flaws of the Manual Clinical Examination", Arthroscopy, Jul. 2010, pp. 997-1004, vol. 26, No. 7.

Examination Report in co-pending European Patent Application No. 13 774 279.7, dated Jul. 2, 2018, 4 pages.

* cited by examiner

1000

1500

1000

5300

ROBOTIC KNEE TESTING (RKT) DEVICE HAVING DECOUPLED DRIVE CAPABILITY AND SYSTEMS AND METHODS PROVIDING THE SAME

CROSS-REFERENCE TO RELATED APPLICATION

This application is a continuation of U.S. application Ser. No. 14/029,780, filed Sep. 17, 2013, and entitled "Robotic Knee Testing (RKT) Device Having Decoupled Drive Capability and Systems and Methods Providing The Same," which, in turn, claims priority to and the benefit of U.S. Provisional Application Ser. No. 61/702,105, filed Sep. 17, 2012, the contents of which are hereby incorporated herein by reference in their entirety.

BACKGROUND

Field of Invention

This generally relates to three-dimensional joint motion evaluation using computer-controlled torque application via, for example, a robotic knee testing device (an "RKT" device) which controls the direction, rate, and magnitude of forces applied in at least three directions. The respective forces are configured to evaluate "IE" (internal-external) movement about a Z-axis of rotation distal to the foot, varus-valgus conditions about a Y-axis of rotation distal to the foot, and "AP" (anterior-posterior) movement of the tibia through a proximal tibia contact arm which rotates about a X-axis of rotation distal to the foot.

Description of Related Art

The knee is composed of the femur or thigh bone, the tibia or shin bone and the patella or knee cap. They are connected by fibrous structures called ligaments which allow a certain amount of 'joint play' or motion to exist between the bone structures. When this 'joint play' is increased or decreased, an abnormal or pathological condition exists in the knee. Attempts have been made in the past to quantify this increase or decrease in 'joint play' of the knee with limited success.

An injury to the knee can cause damage to one or more of the structures of the knee causing an increase in the 'joint play' or motion of the knee. This increase in 'joint play' can create the sensation to the patient that the knee is slipping or 'coming out of joint'. Commonly, this sensation described by the patient is referred to as the feeling of 'joint instability'. The ability of the two bones to actually 'come out of joint' is related to the length of the fibrous structures or ligaments which connect the two bones together as well as the shape and size of the two bones (or three). The ability of the bones to 'come out of joint' or become unstable is related to the amount of stretch or the amount of increased lengthening of each ligament, the number of ligaments involved, and damage to other support structures of the knee such as the bone itself and the menisci. Accurate measurement of this increased ligament length can be critical to restore the knee to as close to its original functional and anatomical state as possible.

Currently, there are only manual tests used by clinicians to aid in the diagnosis of ligament damage resulting in a change in joint play. As an example, there are three manual tests to evaluate the increased joint play associated with an ACL tear—the Lachman's test, the Pivot Shift test and the Anterior Drawer Test. All of these tests suffer from the clinician's subjective evaluation of both the extent of the ligament lengthening and the change in the compliance or stretchiness of the ligament.

The Lachman's test is performed by laying the patient in a supine position and bending the knee at approximately 20 to 30 degrees. The clinician places a hand on the patient's upper thigh and his other hand below the upper part of the patient's calf. Pressure is applied under the patient's calf and down on the patient's thigh such that there is a translation between the femur and the tibia.

Similar to the Lachman's test, the pivot shift test begins by positioning the patient on his back. The knee is placed in full extension (x-axis rotation) and a valgus (y-axis rotation) force and an internal rotation (z-axis rotation) force is applied to the knee to allow the lateral tibia to slip anteriorly from underneath the lateral femoral condyle as the knee is flexed (x-rotation) the tibia is allowed to slip suddenly back underneath the femoral condyle. The clinician feels for an abnormal external rotation (z-axis rotation) and posterior translation (y-axis translation) of the tibia with respect to the femur. This shift is felt to represent the relative increased translation (y-axis translation) of the lateral side of the knee with respect to the increased translation (y-axis translation) of the medial side of the knee. Furthermore, the point of sudden shift represents the point at which the tibia bone slides from in front of the radius of curvature of the curved end of the femur back to its normal position under the femoral condyle. The clinician subjectively rates the pivot shift as Grade I, Grade II or Grade III depending upon the degree of rotational and translational shift felt during the test. This test is difficult to perform, difficult to teach and difficult to quantify.

Finally, the anterior drawer test is performed with the patient lying on his back and his knee bent 90 degrees. With the patient's foot supported by a table or chair, the clinician applies pressure to the knee using her thumbs. This test is graded based on the amount or extent of anterior translation of the tibia with respect to the femur. Grade I has 0 to 5 mm of anterior translation Grade II has 6 to 10 mm of anterior translation, and Grade III has 11 to 15 mm of anterior translation.

To diagnose an injured ACL using the described tests, the clinician must determine whether the knee feels "abnormal." Thus, the accuracy of an ACL injury diagnosis using currently known tests depends on the skill and experience of the clinician. A misdiagnosis can lead to unnecessary delay in treatment, thereby placing the patient at increased risk for further damage to the knee.

There are manual tests for the LCL, MCL and the PCL. Each manual test relies on grading the ligament lengthening based upon relative increase in joint play into three categories. There is no effort to grade the compliance of the ligament; however, the expert clinician will describe the ligament in terms of its 'feel'. The more ligaments and structures that are damaged; the more complex it becomes to perform a manual knee examination with accuracy.

There have been multiple attempts in the past to instrument the knee and quantify or measure the change in the structure of the knee after ligament damage. Several devices have attempted to accurately quantify the extent or relative displacement and compliance of a ligament in the knee. One of these devices is The KT-1000 and the KT-2000 Medmetric®, which measures the anterior-posterior translation of the tibia with respect to the femur along the y-axis, but disadvantageously attach to the tibia. These devices attempt to quantify the findings found when the clinician uses the Lachman's test and the Anterior Drawer Test. Force is applied to a handle on the device which measures force and signals to the clinician the amount of force with a low pitched sound for a 15 pound force and a higher pitched sound for a 20 pound force. This force pulls anteriorly along the y-axis through a strap that wraps underneath the calf. The measurement of the translation uses a technique measuring the relative motion of a pad on the anterior tibia with respect to a pad placed on the patella. This device does not measure relative displacement or compliance in any of the other degrees of freedom previously described in the knee. Furthermore, the quantified results of the KT-1000 or KT-2000 have not been correlated with patient satisfaction whereas the subjective Pivot Shift test has been correlated with patient satisfaction. Other devices such as the Stryker KLT, the Rolimeter, and the KSS system use similar mechanisms to attempt to quantify the normal amount of 'joint play' or motion between the femur and tibia, along with any increased 'joint play' or motion which is associated with ligament lengthening and damage.

Many non-invasive systems utilize sensors or markers that are attached to the skin, including but not limited to optoelectronic, ultrasonic, and electromagnetic motion analysis systems. These skin sensors or markers are merely representations of location of the underlying bones; however, many published reports have documented the measurement error related to skin artifact with this system. In order to avoid the inaccuracies associated with skin artifact, medical imaging systems may be utilized in order to precisely determine the position/location of the bones accurately.

Surgeons manually examine the joint for altered play; however, due to the variability in size of the patient, size and experience of the surgeon, and the subtlety of injury, consistent and reproducible reports of joint play between surgeons is not possible. The need that must be met is to provide a controlled application of torque during joint examination, with the magnitude, direction, and rate of torque application being controlled. Many reports have documented that, whether performed by hand or with manual arthrometers, the manual application of torque varies between clinicians, thus creating inconsistencies in the examination of joint play.

Accordingly, there is a need for an accurate, objective, reliable and reproducible measure of the impact of damage to the ACL as well as other ligaments and structures in the knee or combination of ligaments and other structures in the knee that can be used in the clinical setting on patients. For example, since an injury to the ACL produces both an increase in anterior translation (y-axis translation) and rotation (z-axis rotation), an objective measure of these changes would both aid in the diagnosis of the injury as well as verify its restoration after ligament reconstruction surgery. Additionally, measurement of displacement and compliance around different degrees of freedom in the knee would help objectively describe the individual and complex changes to 'joint play' that occurs in an injured knee with structural damage. A need exists for systems and methods that can provide accurate, reproducible and objective data on the changes in 'joint play' or motion that occurs with an injured knee compared to their healthy knee and to the population as a whole such that the clinician can achieve patient satisfaction with focused, biomechanical and proven surgical interventions specific to that injury and for that knee across the entire population of damaged knees.

Needs also exist for systems and methods, and devices which accommodate variances of patient body structure; it may well be understood that each human body is different and may require particular attention when being treated and/or analyzed; this may be particularly evident in the case of abnormalities of bones, tendons, joints, etc., due to injury or the like. Needs also exists for systems and methods, and devices that can provide the type of accurate, reproducible and objective data described above without inherently and/or indirectly adversely impacting the accuracy, reproducibility, and/or objectiveness of the tests and measured data therein.

SUMMARY

Generally described, the present invention to provide apparatuses and methods for evaluating the performance of joints and their associated elements, as described elsewhere herein.

According to various embodiments a limb manipulation and evaluation device including three drives is provided. The device comprises: a first drive configured to manipulate a first bone relative to a second bone in a first direction; a second drive configured to manipulate the first bone relative to the second bone in a second direction; and a third drive configured to manipulate the first bone relative to the second bone in a second direction. The first, second, and third directions are different relative to each other, and at least one of the drives is mutually decoupled relative to another drive, such that operation of the one drive does not affect the position or movement of the another drive.

According to various embodiments a limb manipulation and evaluation device including three drives is provided. The device comprises: a first drive configured to manipulate a first bone relative to a second bone about a first axis; a second drive configured to manipulate the first bone relative to the second bone about a second axis; and a third drive configured to manipulate the first bone relative to the second bone about a third axis, wherein: the first, second, and third axes are each oriented at an angle relative to each other, and at least one of the drives is mutually decoupled relative to another of the drives, such that operation of the one drive does not affect the rotational axis of the another of the drives.

According to various embodiments a limb manipulation and evaluation device including three drives is provided. The device comprises: a first drive configured to manipulate a first bone relative to a second bone about a first axis, a second drive configured to manipulate the first bone relative to the second bone about a second axis, and a third drive configured to manipulate the first bone relative to the second bone about a third axis, wherein: the first, second, and third axes are each oriented at an angle relative to each other, and at least two of the drives are decoupled relative to a third drive, such that operation of either of the two drives does not affect the rotational axis of the third drive.

According to various embodiments a limb manipulation and evaluation device including three drives is provided. The device comprises: a first drive configured to manipulate a first bone relative to a second bone about a first axis, a second drive configured to manipulate the first bone relative to the second bone about a second axis, and a third drive configured to manipulate the first bone relative to the second bone about a third axis, wherein: the first, second, and third axes are each oriented at an angle relative to each other, and at least one of the drives is mutually decoupled relative to the other two drives, such that operation of the at least one drive does not affect the rotational axis of the other two drives.

According to various embodiments a limb manipulation and evaluation device including three drives is provided.

The device comprises: a first drive configured to manipulate a tibia relative to a femur about a first axis, the first drive providing internal and external rotation of the tibia relative to the femur; a second drive configured to manipulate the tibia relative to the femur about a second axis, the second drive providing anterior-posterior movement of the tibia relative to the femur, and a third drive configured to manipulate the tibia relative to a femur about a third axis, the third drive providing valgus-varus movement of the tibia relative to the femur, wherein: the first, second, and third axes are each oriented at an angle relative to each other; the first drive is decoupled from the second drive; and the first and second drives are coupled with the third drive.

According to various embodiments a limb manipulation and evaluation device including three drives is provided. The device comprises: a first drive configured to manipulate a tibia relative to a femur about a first axis, the first drive providing internal and external rotation of the tibia relative to the femur; a second drive configured to manipulate the tibia relative to the femur about a second axis, the second drive providing anterior-posterior movement of the tibia relative to the femur, and a third drive configured to manipulate the tibia relative to a femur about a third axis, the third drive providing valgus-varus movement of the tibia relative to the femur, wherein: the first, second, and third axes are each oriented at an angle relative to each other; the first drive is coupled to the third drive; the second drive is decoupled from the first and third drives; and the third drive is decoupled from the first and second drives.

According to various embodiments a method of using three drives to manipulate a first bone relative to a second bone is provided. The method comprises the steps of: operating a first drive configured to manipulate the first bone relative to the second bone about a first axis; operating a second drive configured to manipulate the first bone relative to the second bone about a second axis; and operating a third drive configured to manipulate the first bone relative to the second bone about a third axis, wherein: the first, second, and third axes are each oriented at an angle relative to each other, and the operation of at least one of the drives is mutually decoupled relative to another of the drives, such that the operation of the one drive does not affect the rotational axis of the another of the drives.

BRIEF DESCRIPTION OF THE DRAWINGS

Figure 1:
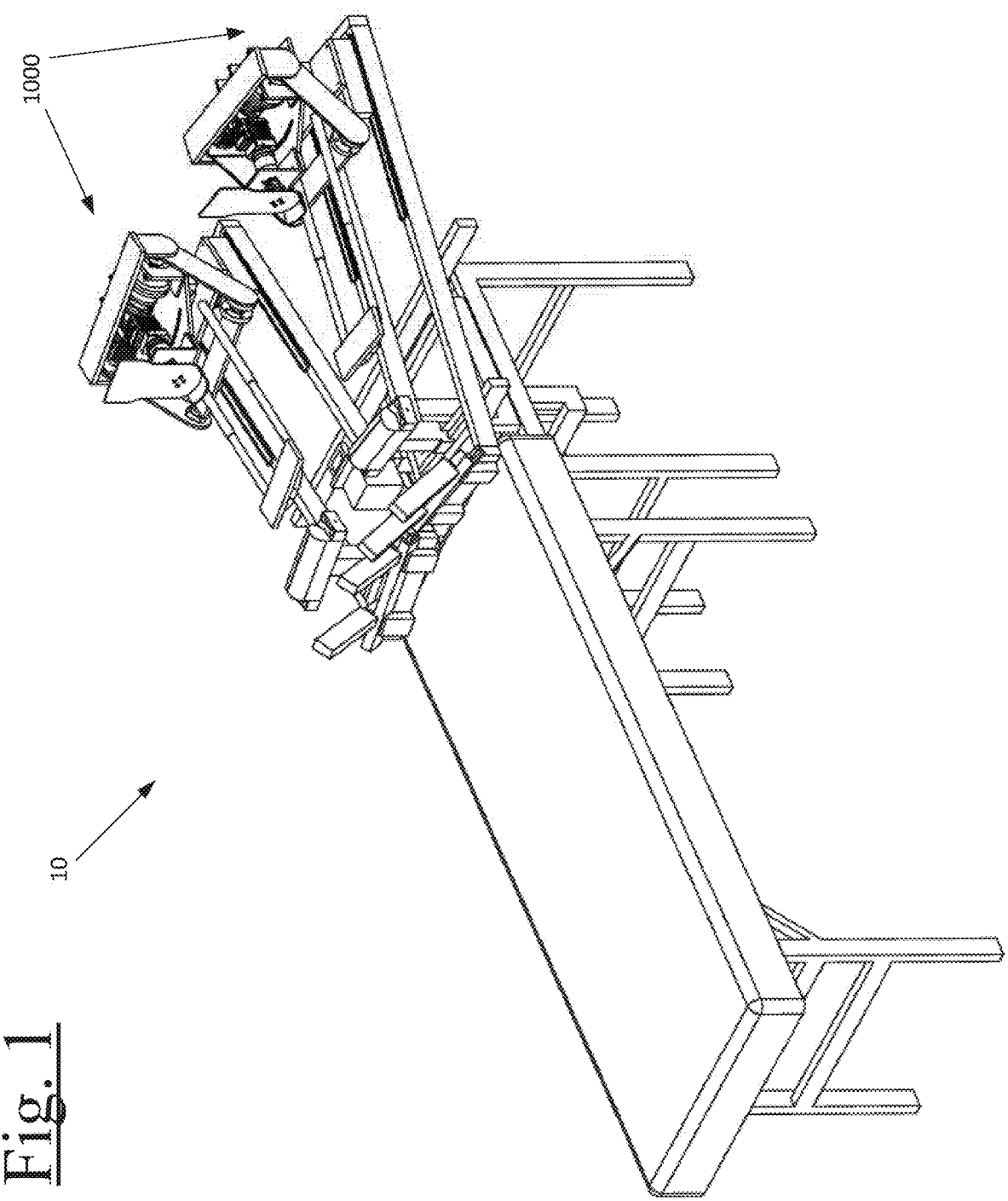
Figure 2:
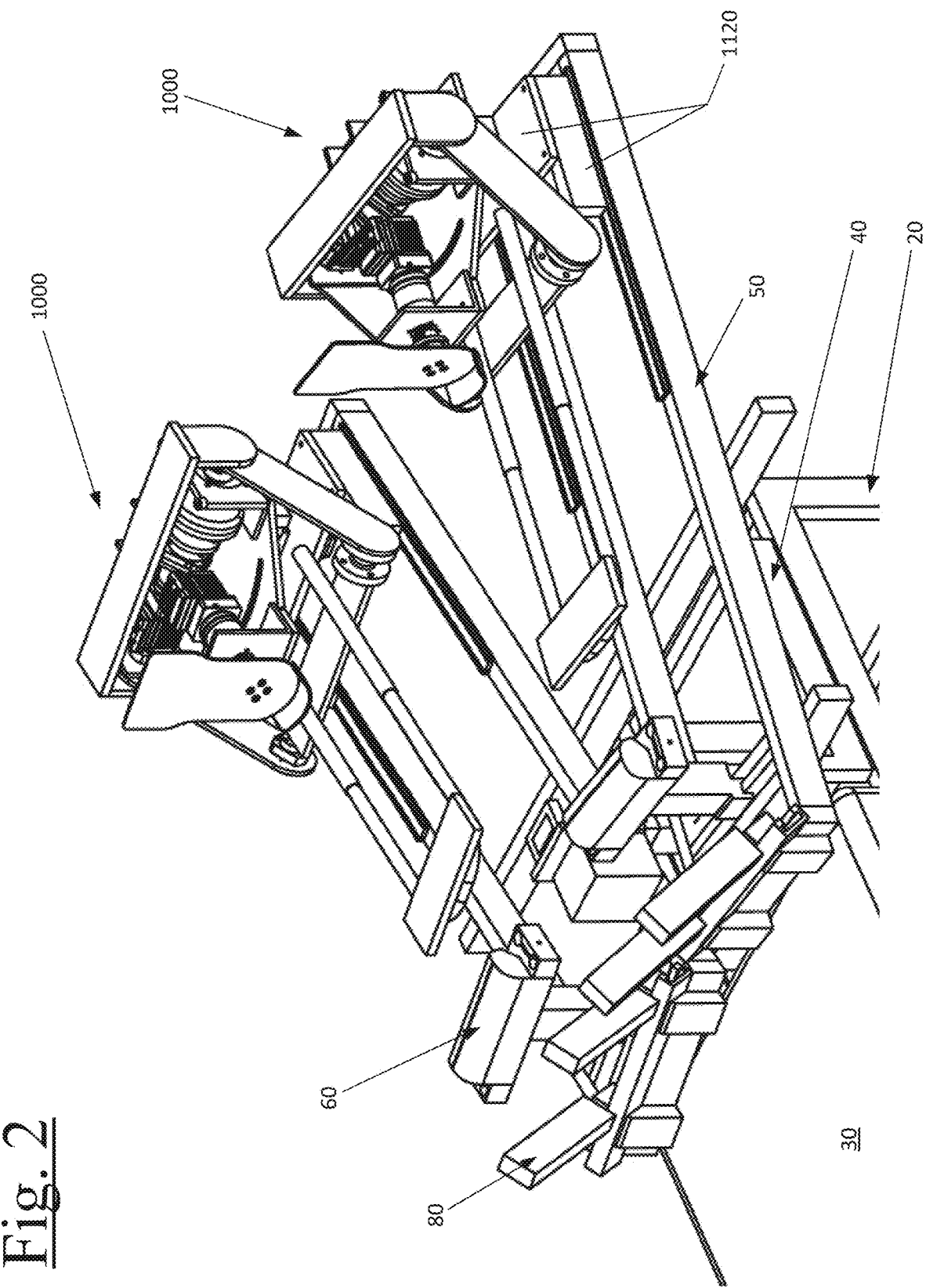
Figure 3:
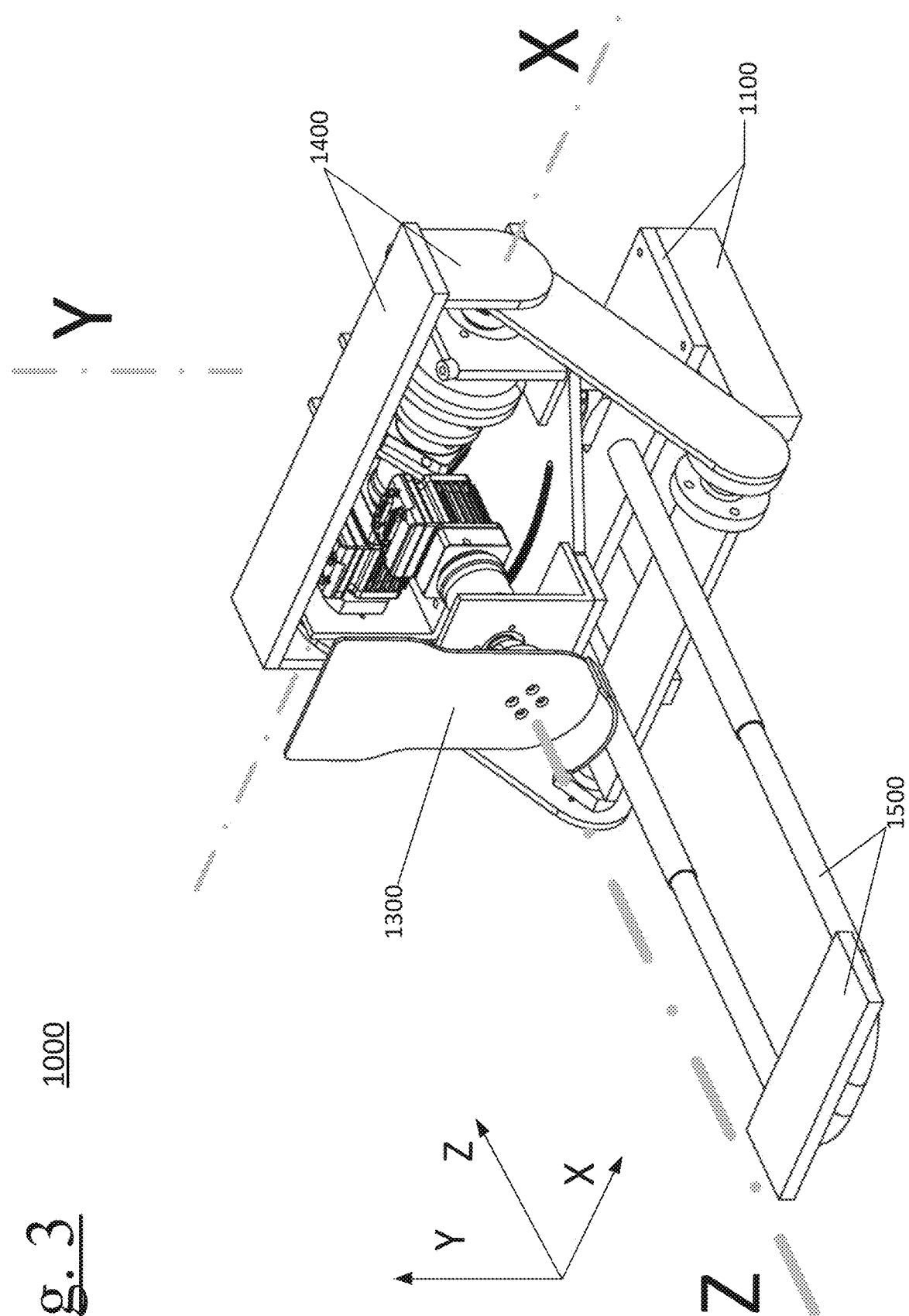
Figure 4:
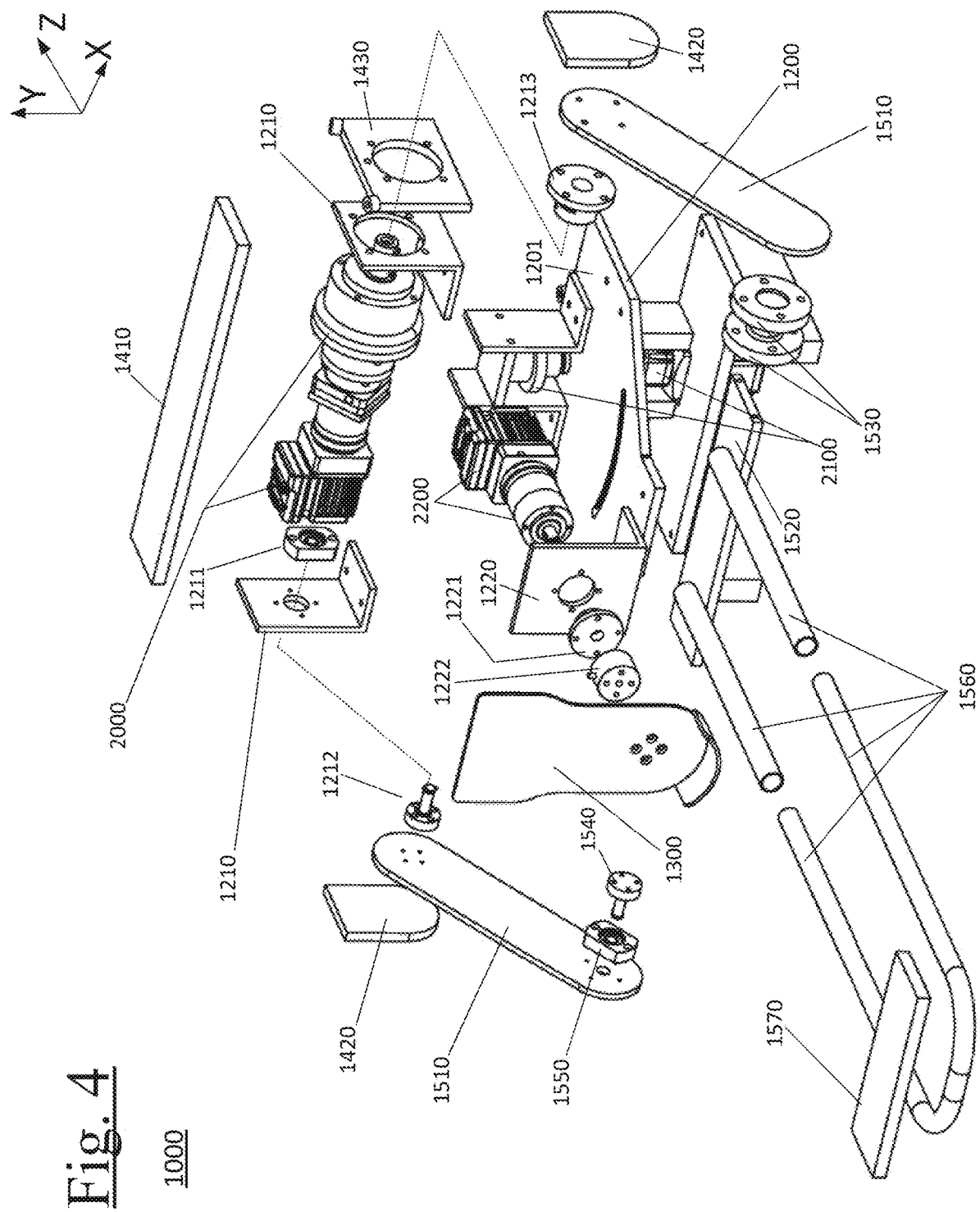
Figure 5:
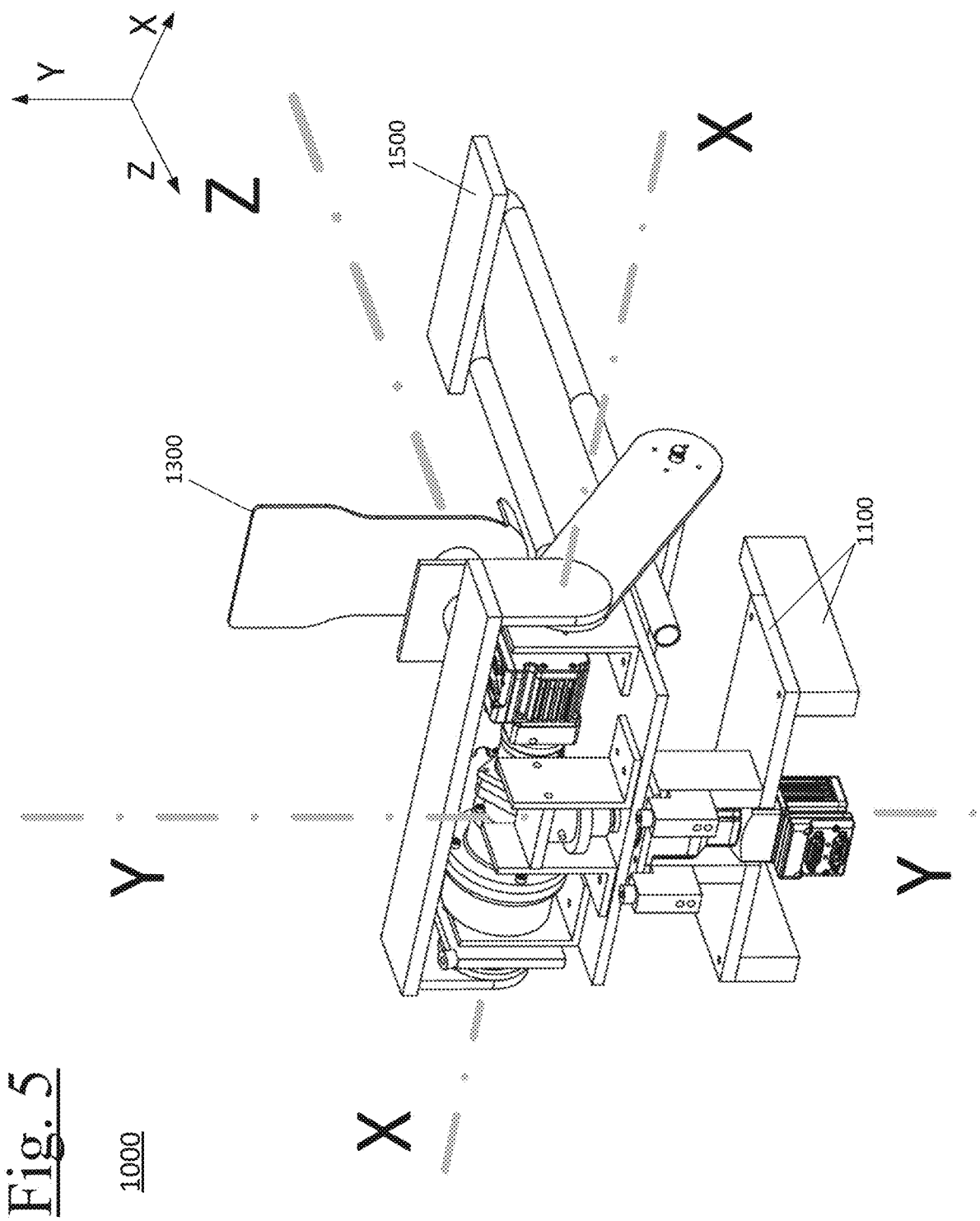
Figure 6:
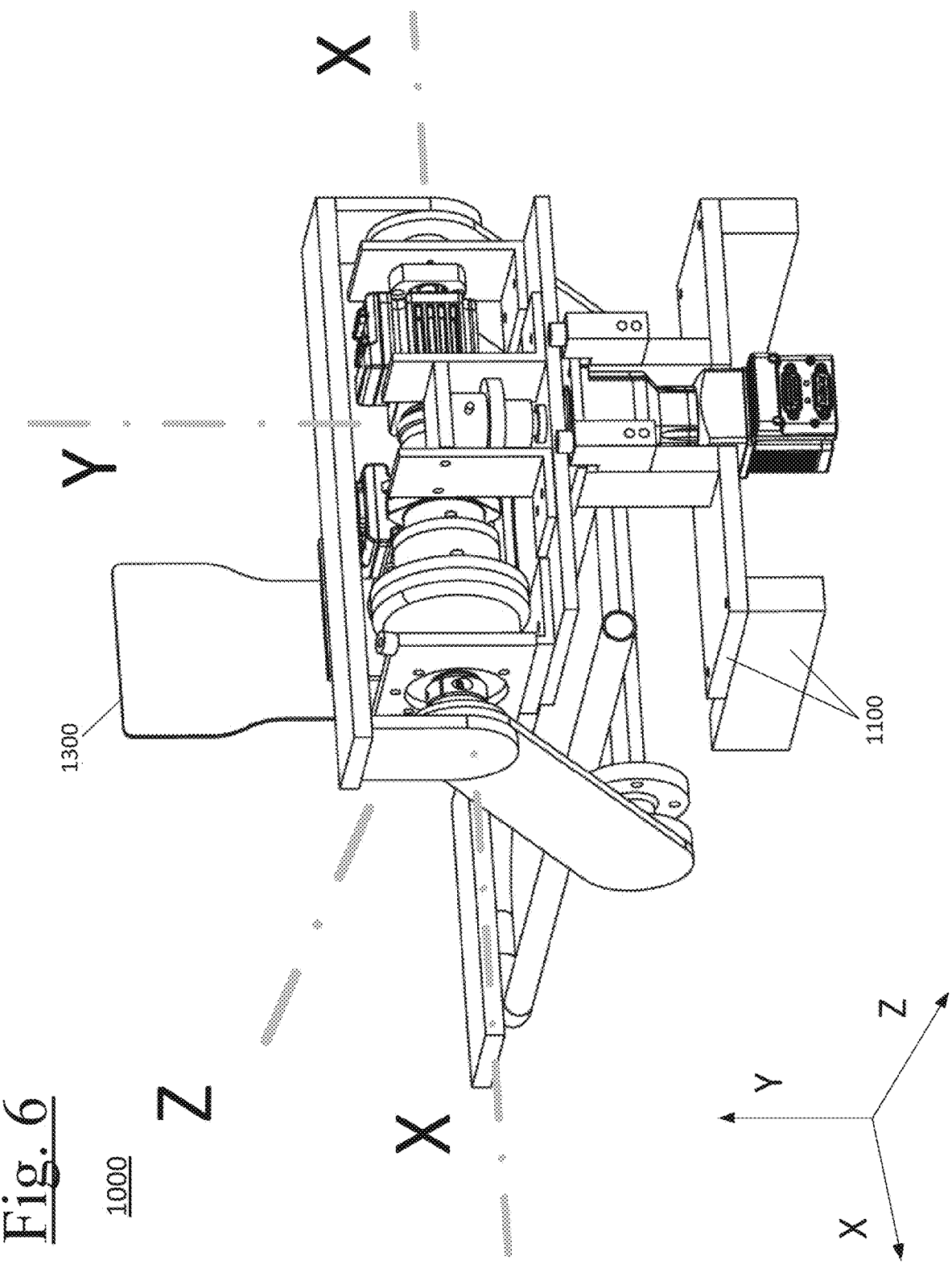
Figure 7:
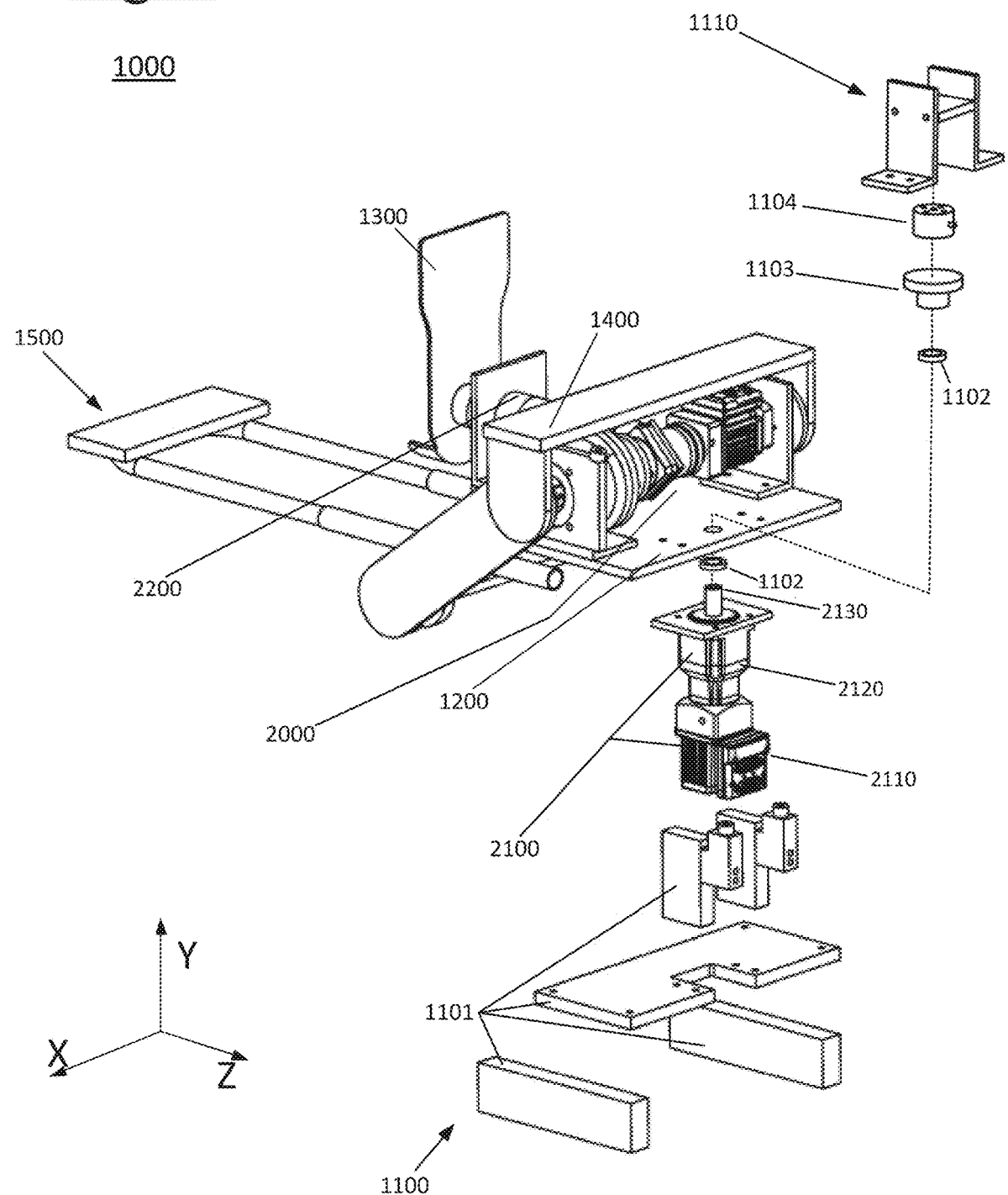
Figure 8:
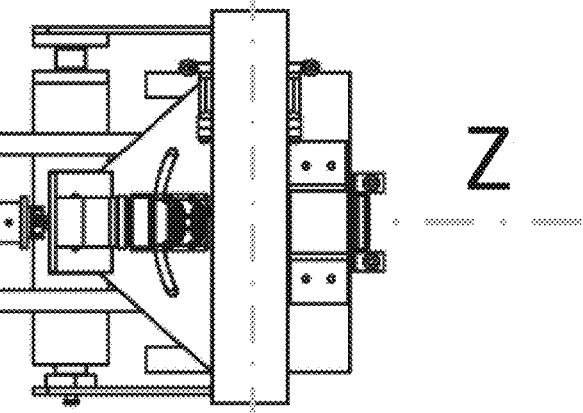
Figure 9:
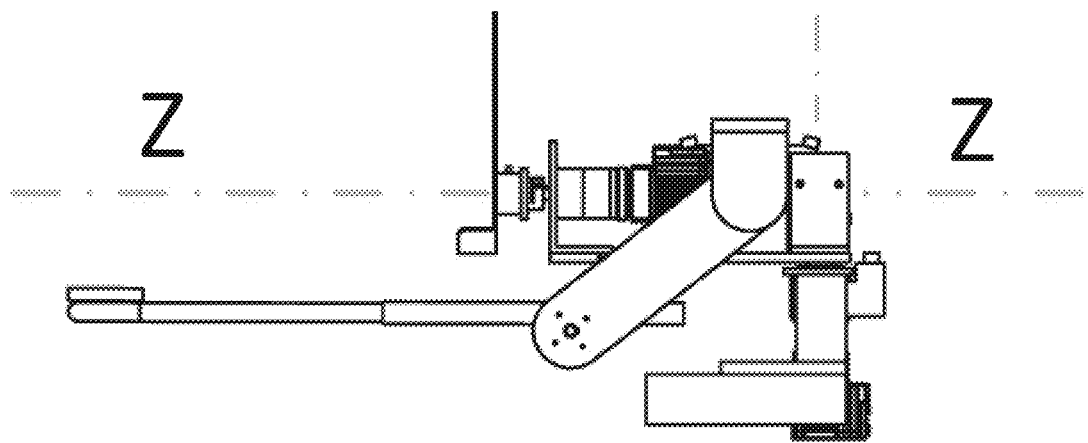
Figure 10:
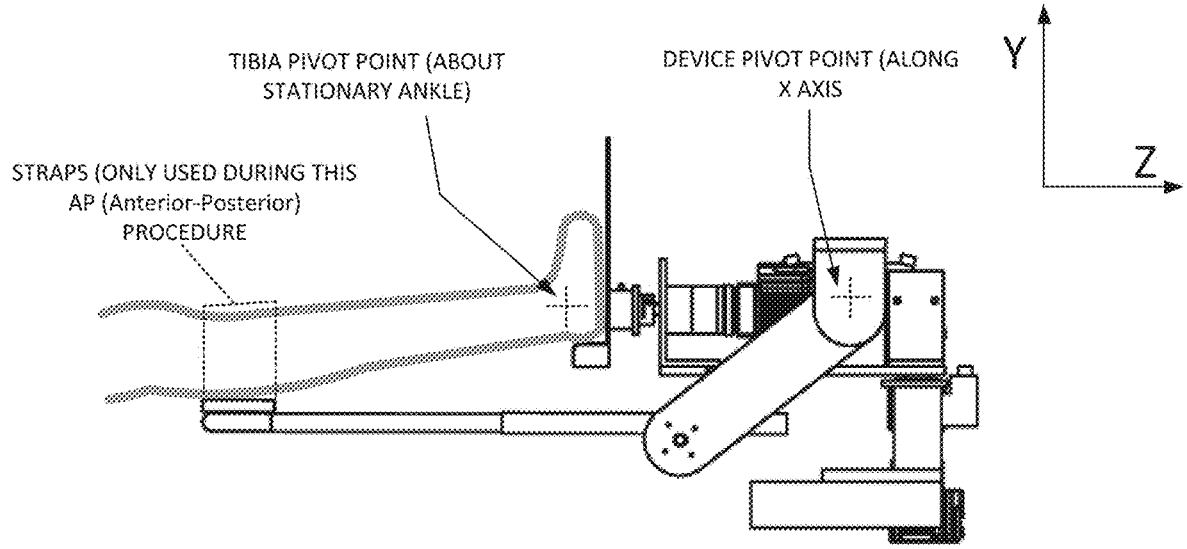
Figure 11:
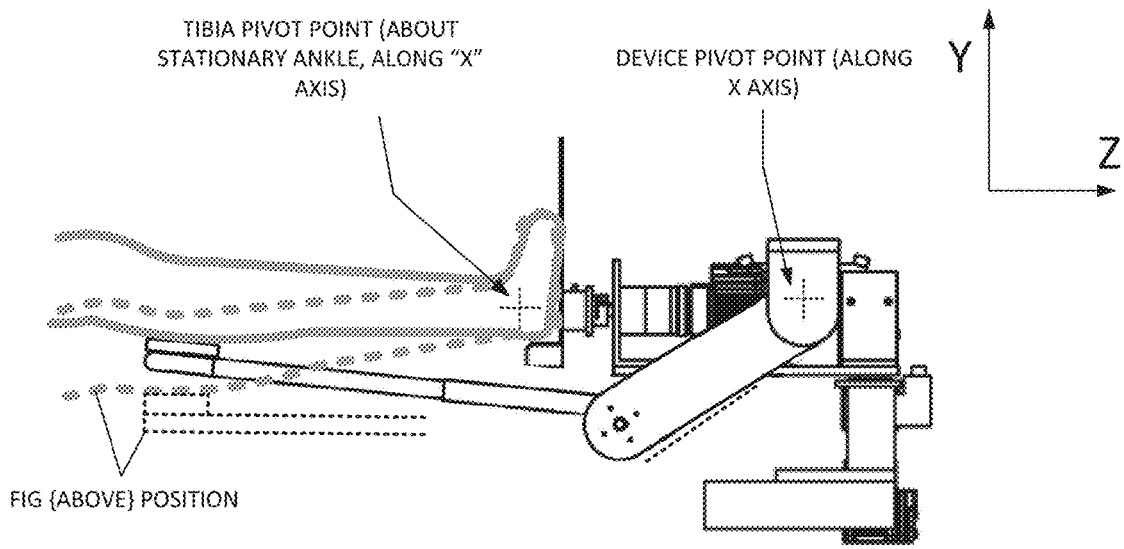
Figure 12:
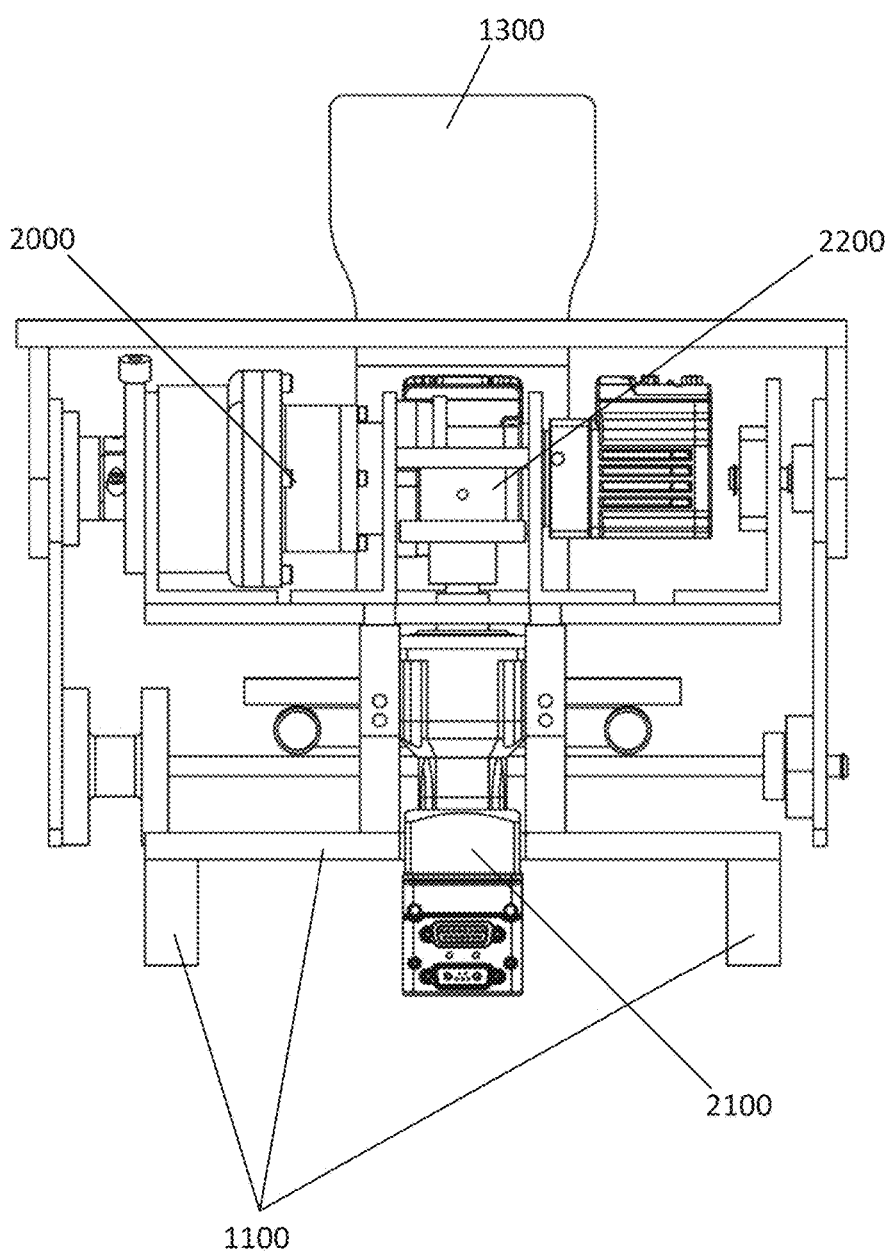
Figure 13:
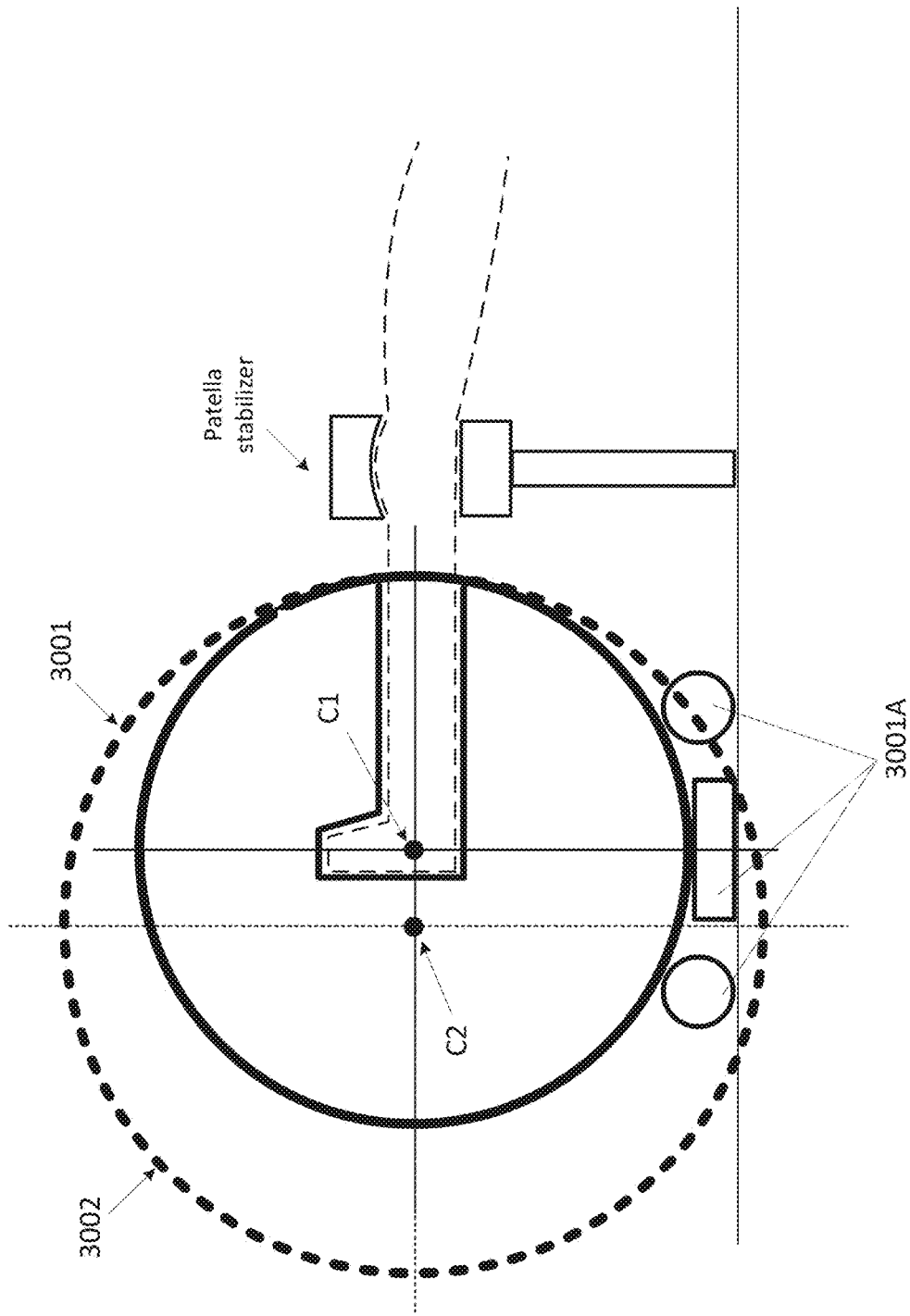
Figure 14:
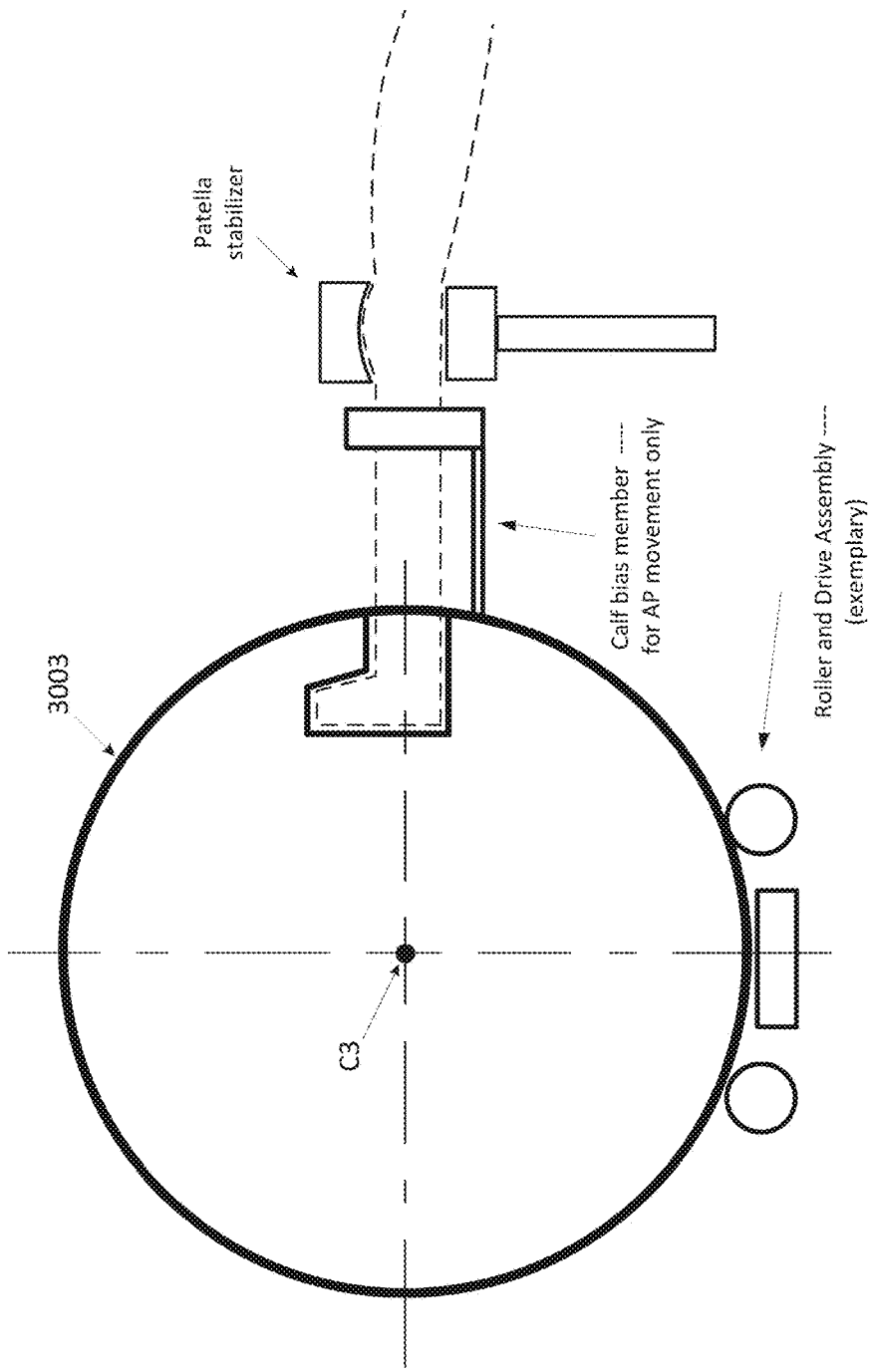
Figure 15:
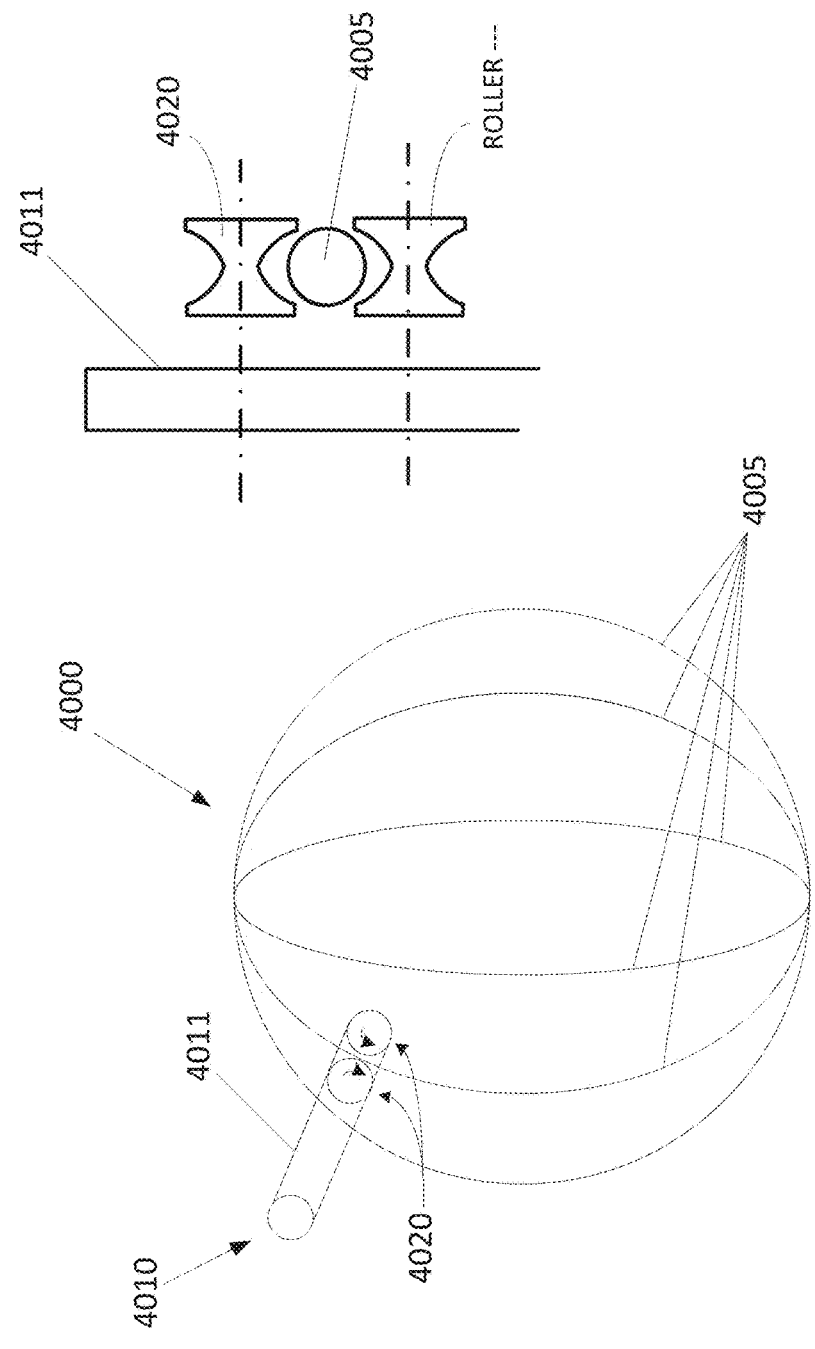

Having thus described the invention in general terms, reference will now be made to the accompanying drawings, which are not necessarily to scale. In the drawings:

FIG. 1 is a perspective view of the overall device 10, including two tibia positioning assemblies 1000 according to various embodiments;

FIG. 2 is a view of a portion of FIG. 1, and in particular illustrates a perspective view of the two tibia positioning assemblies 1000 according to various embodiments;

FIG. 3 is an isolated view of one of the two tibia positioning assemblies 1000 according to various embodiments;

FIG. 4 is an exploded view of the various elements of the tibia positioning assembly 1000 of FIG. 3 according to various embodiments;

FIG. 5 is a view of the tibia positioning assembly 1000 of FIG. 3, but from an alternative facing perspective relative to that of FIG. 3, illustrating exemplary axes X, Y, and Z of rotation, along with calf bias assembly 1500 according to various embodiments;

FIG. 6 is yet another view of the tibia positioning assembly 1000 of FIGS. 3 and 5, also illustrating an exemplary foot plate assembly 1300 according to various embodiments;

FIG. 7 is an exploded view of the various element of a sliding frame assembly 1100 and a "Y" axis drive assembly 2100 of the tibia positioning assembly 1000 of FIG. 3 according to various embodiments;

FIG. 8 is a top plan view of the tibia positioning assembly 1000 of FIG. 3, in an exemplary "right leg" configuration according to various embodiments;

FIG. 9 is a side view of the tibia positioning assembly 1000 of FIG. 8 according to various embodiments;

FIGS. 10 and 11 illustrate two sequential steps of movement of the device during operation of a "X" axis drive assembly 2000 according to various embodiments;

FIG. 12 illustrates a view along the "Z" axis of the tibia positioning assembly 1000 of FIG. 3 according to various embodiments, further illustrating exemplary X, Y, and Z axis drive assemblies 2000, 2100, and 2200 (note that the illustrated "Z" axis extends positive perpendicular to the foot plate extending distal to the foot plate, the illustrated "Y" axis extends positive straight up from "Z" axis and away from floor/ground, and the illustrated "X" axis is parallel to the bottom of the foot plate and is also parallel to the floor/ground according to various embodiments so as to provide three mutually orthogonal axes);

FIG. 13 is an alternate configuration according to various embodiments, illustrating the use of exemplary spherical elements 3001, 3002 for manipulating the lower leg of a patient (shown in dotted line) about centers of the spheres, wherein sphere 3001 is driven by an exemplary roller and drive assembly 3001A;

FIG. 14 is another alternate configuration illustrating the use of an exemplary spherical element 3003 according to various embodiments, with a center of rotation C3 located even further distal to the foot and an exemplary calf bias member (aka extender bar); and FIG. 15 is yet another alternate configuration including a spherical cage 4000 comprised of a plurality of cage bars 4005 according to various embodiments.

Figure 16:
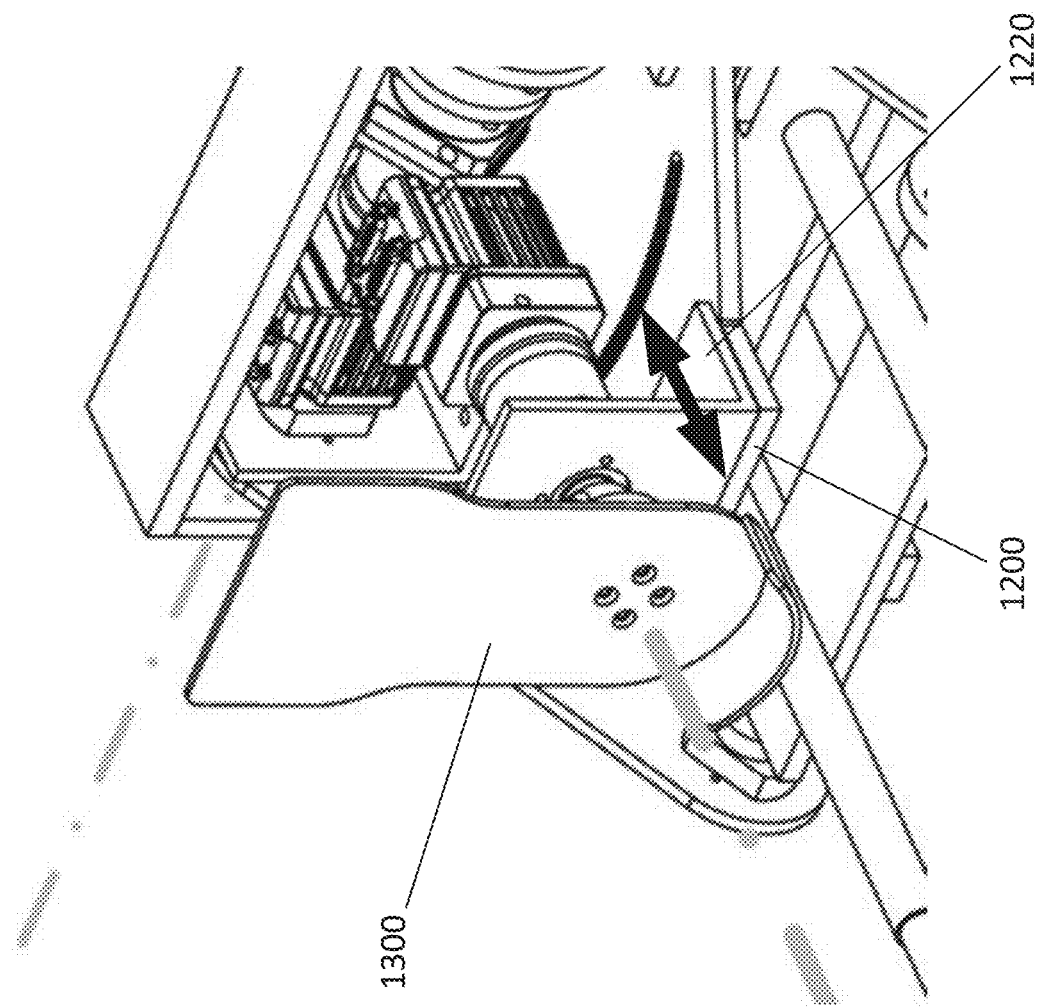

FIG. 16 shows an alternate configuration for the L Bracket 1220, in that L Bracket 1220, which supports the Z Drive motor, can if desired slide along the Z axis relative to pivoting plate assembly 1200 in order to accommodate "pistoning" of foot in varus valgus procedure, allowing for the foot to move in a more natural arc during varus-valgus testing. The foot plate and motor all move together.

Figure 17:
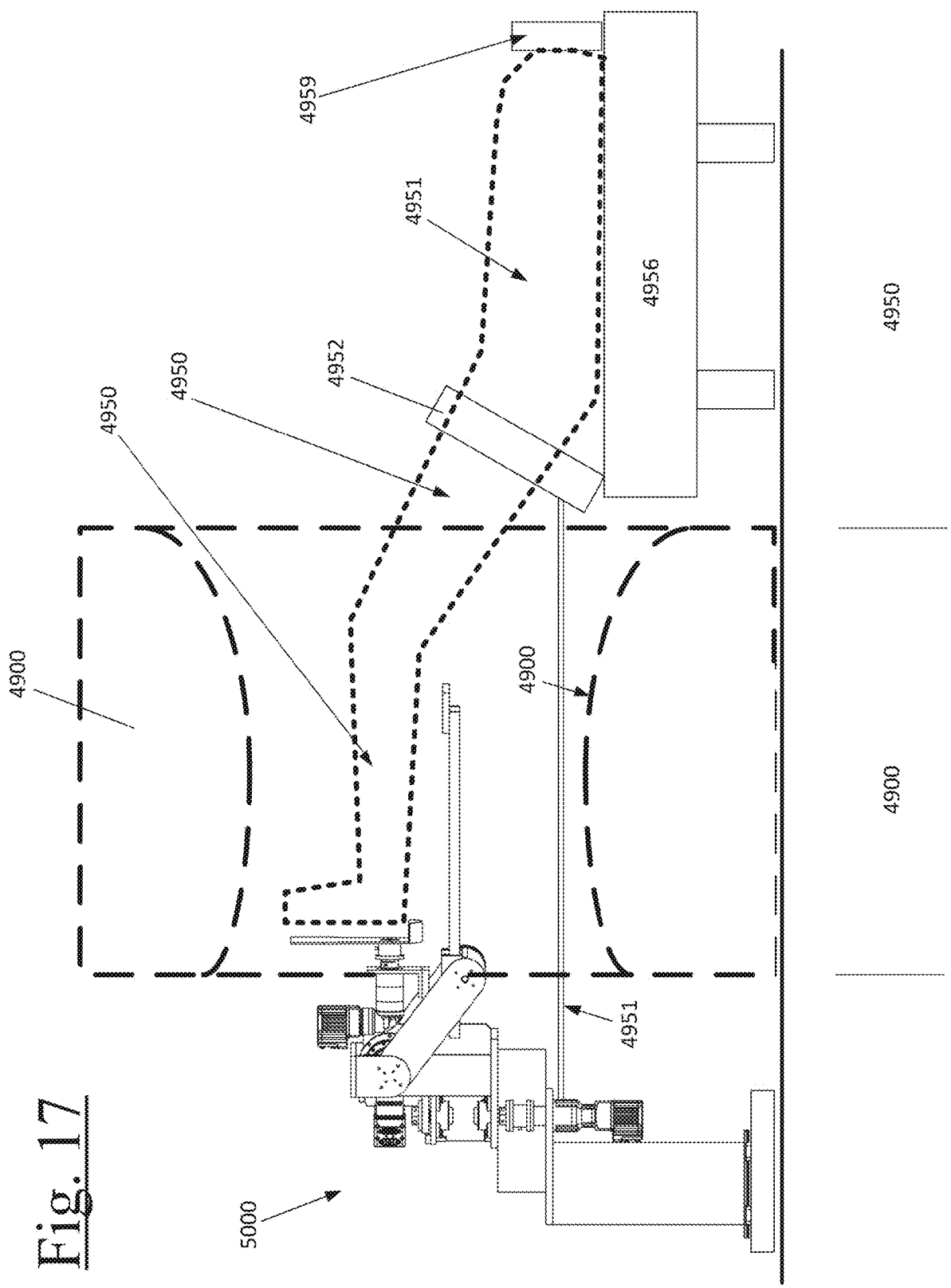

FIG. 17 is a side illustrative view of a leg testing apparatus 5000, in combination with an exemplary CT scanner 4900, and a patient's body support apparatus 4950. The three devices are configured to be typically situated atop an unnumbered supporting surface. Also shown is an exemplary patient, including a patient upper body 4951, patient lower leg 4950, and patient upper leg 4950.

The patient body support apparatus 4950 includes a patient back support 4956, a shoulder restraint 4959, and a thigh restraint 4952.

Figure 18:
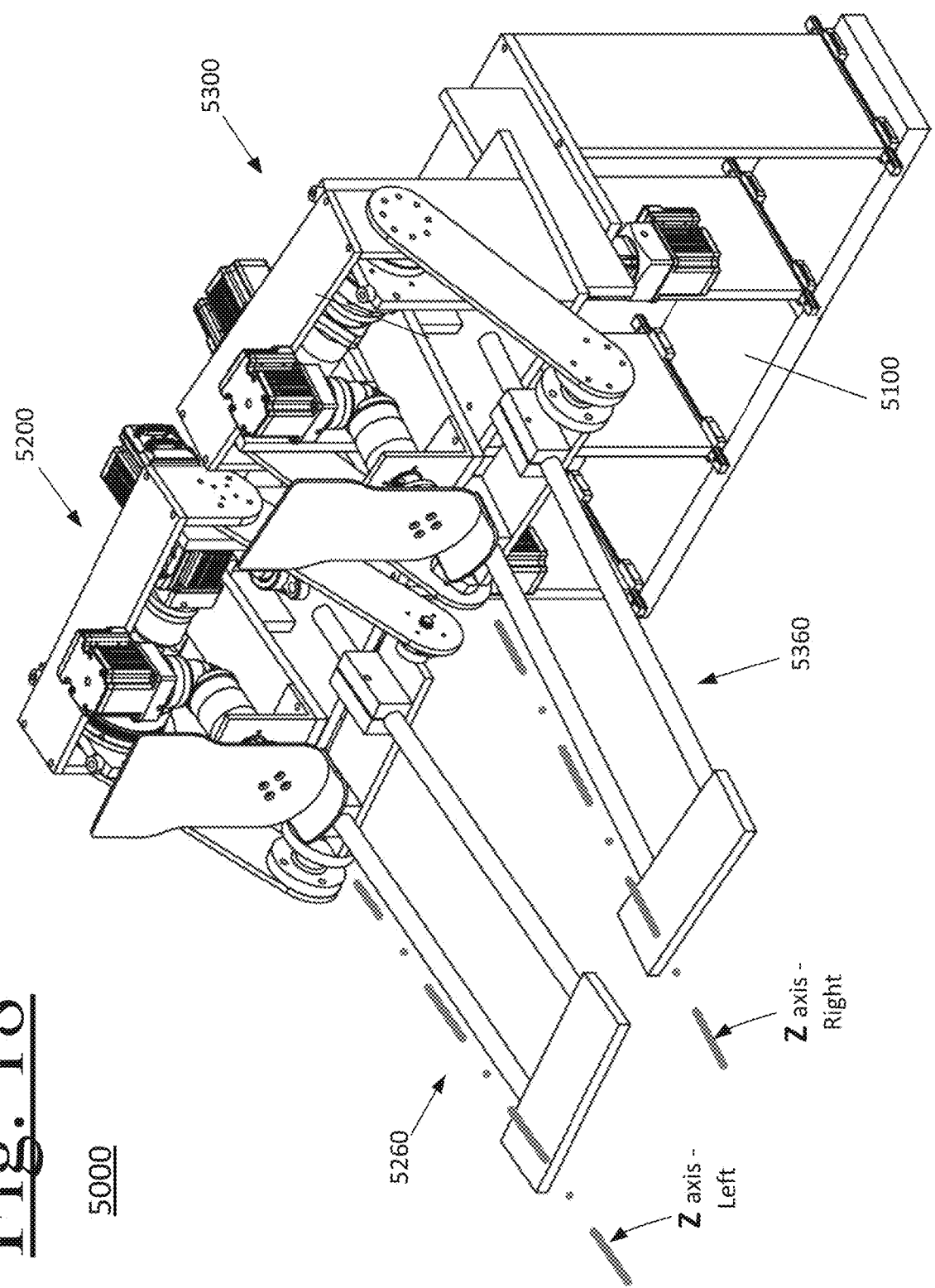

FIG. 18 is a perspective view of a leg testing apparatus 5000 according to one aspect of the present inventions, which includes left lower leg supporting apparatus 5200, right lower leg supporting apparatus 5300, and lower frame number 5100. As may be seen, the "Z" axes of the two apparatuses 5200, and 5300, are not aligned. This will be discussed elsewhere in this application.

Figure 19:
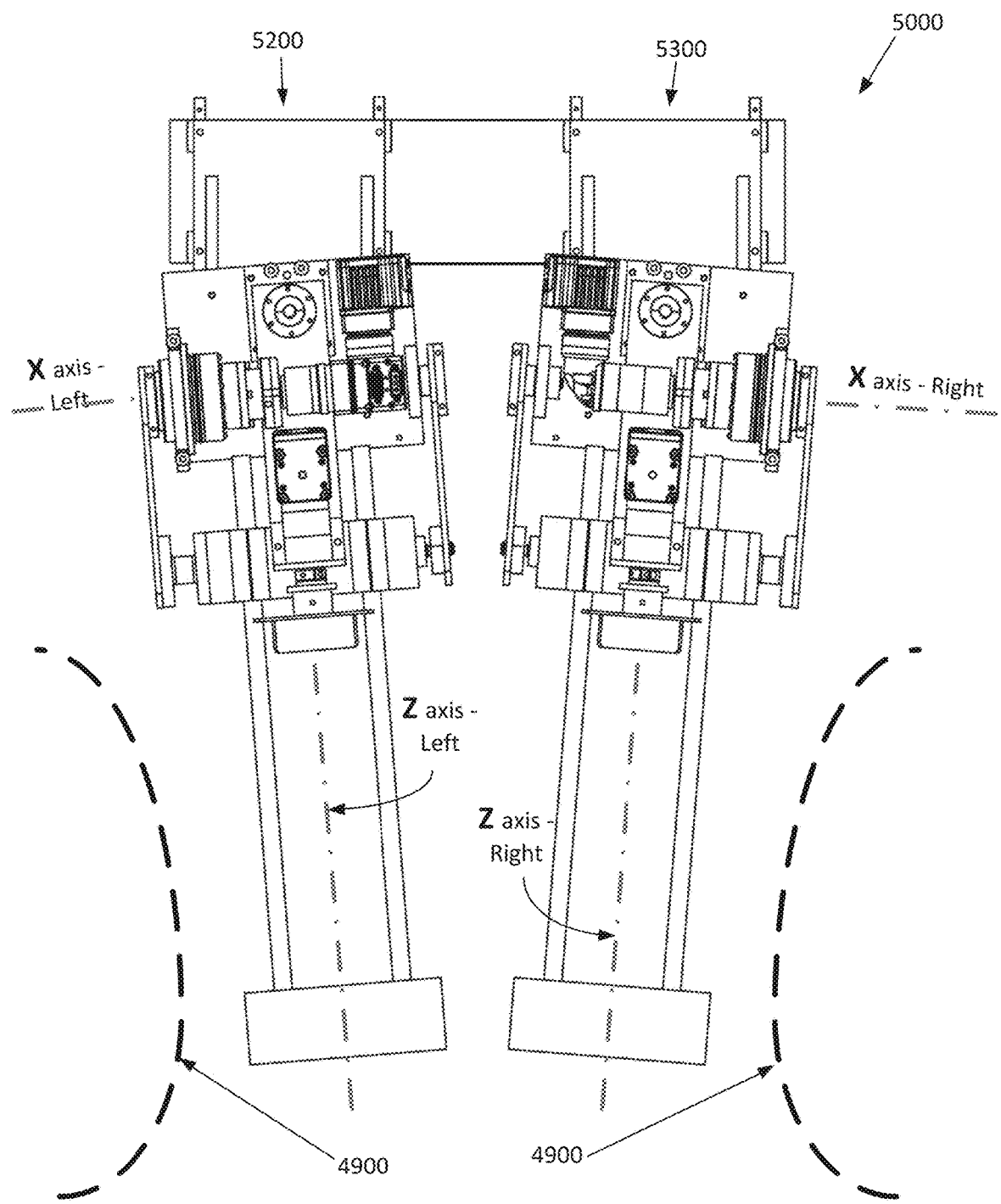

FIG. 19 is a top elevation view of the leg testing apparatus 5000 of FIG. 18, illustrating the relationship of the left lower leg supporting apparatus 5200 and the right lower leg supporting apparatus 5300, relative to the inner surface of the scanning device 4900. As may be seen, the "X" axes of the two apparatuses 5200, and 5300, are also not aligned, and in the embodiment shown, the angle between the two is fixed.

Figure 20:
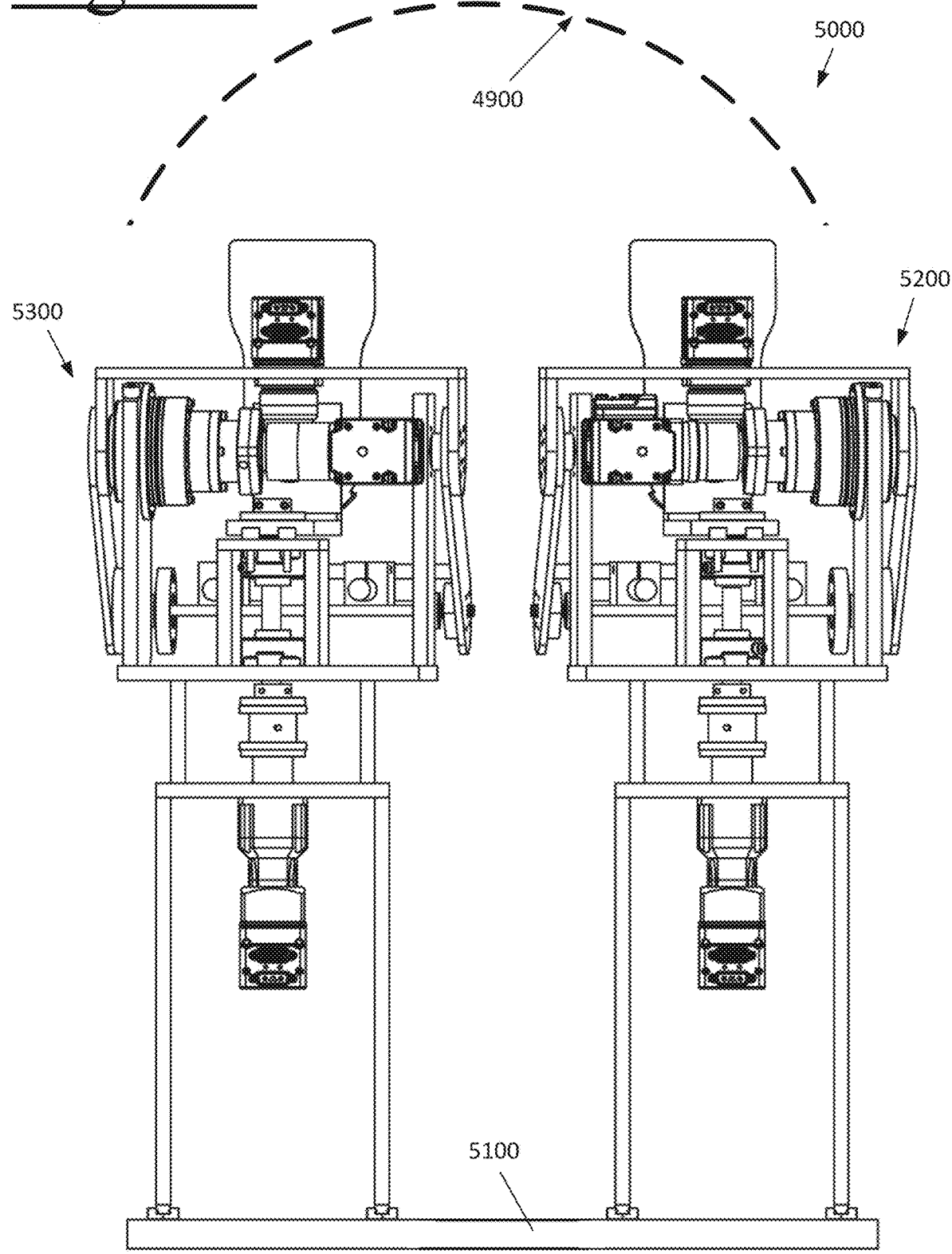

FIG. 20 is a rear elevation view of the leg testing apparatus 5000 of FIG. 18, which includes left lower leg supporting apparatus 5200, right lower leg supporting apparatus 5300, and lower frame number 5100.

Figure 21:
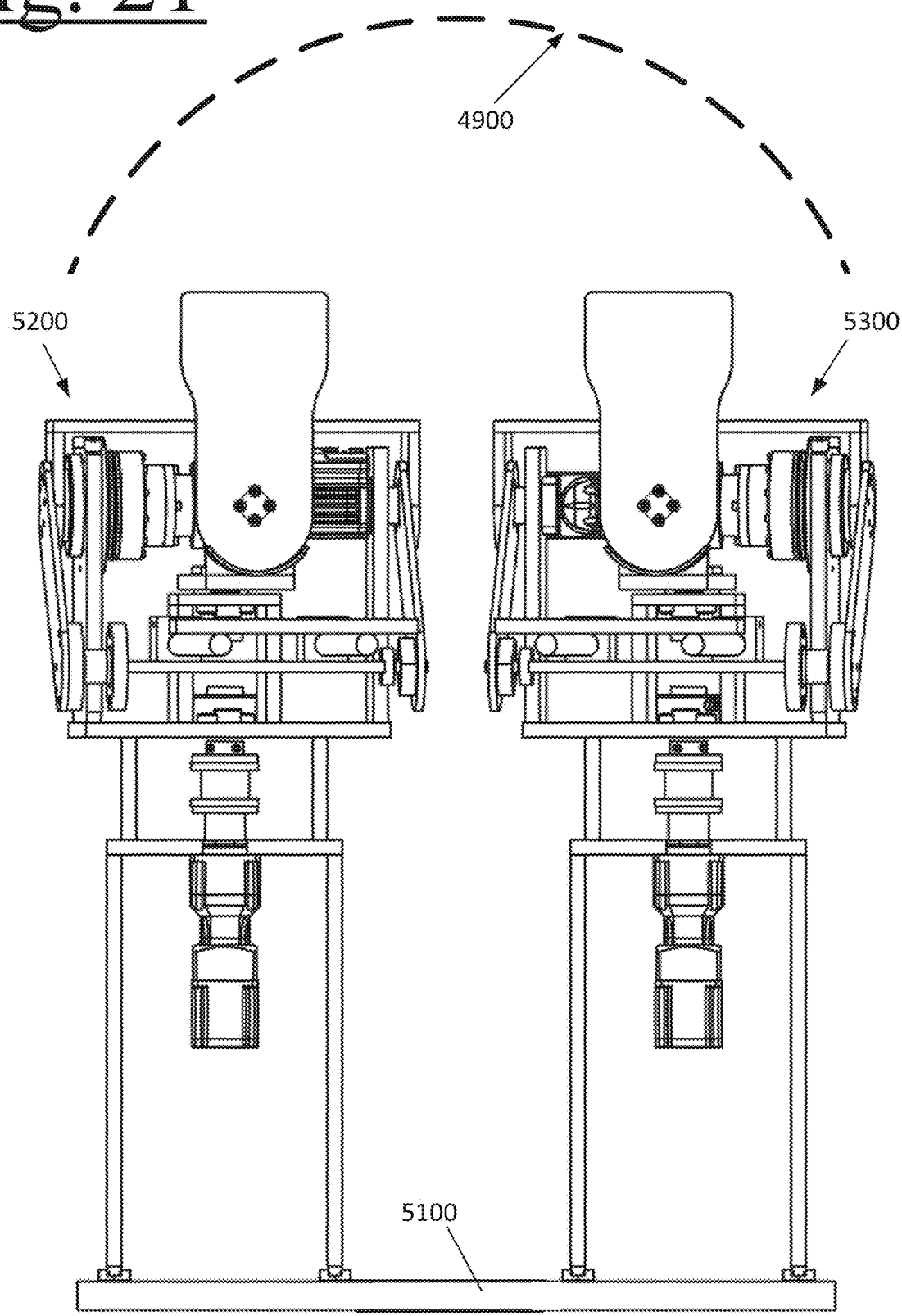

FIG. 21 is a front elevation view of the leg testing apparatus 5000 of FIG. 20.

Figure 22:
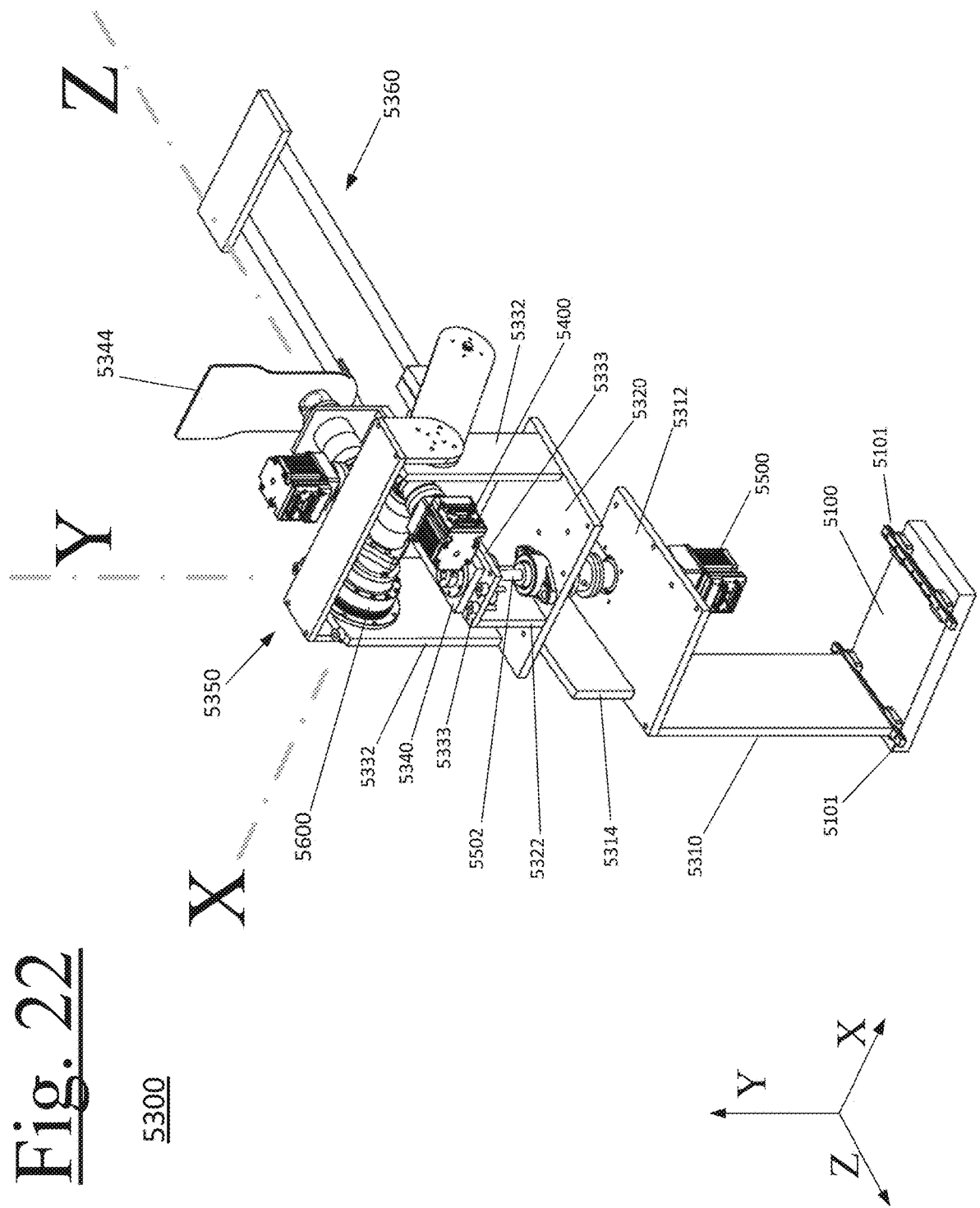

FIG. 22 is a pictorial view of the right lower leg supporting apparatus 5300, with certain elements not included for purposes of explanation.

Figure 23:
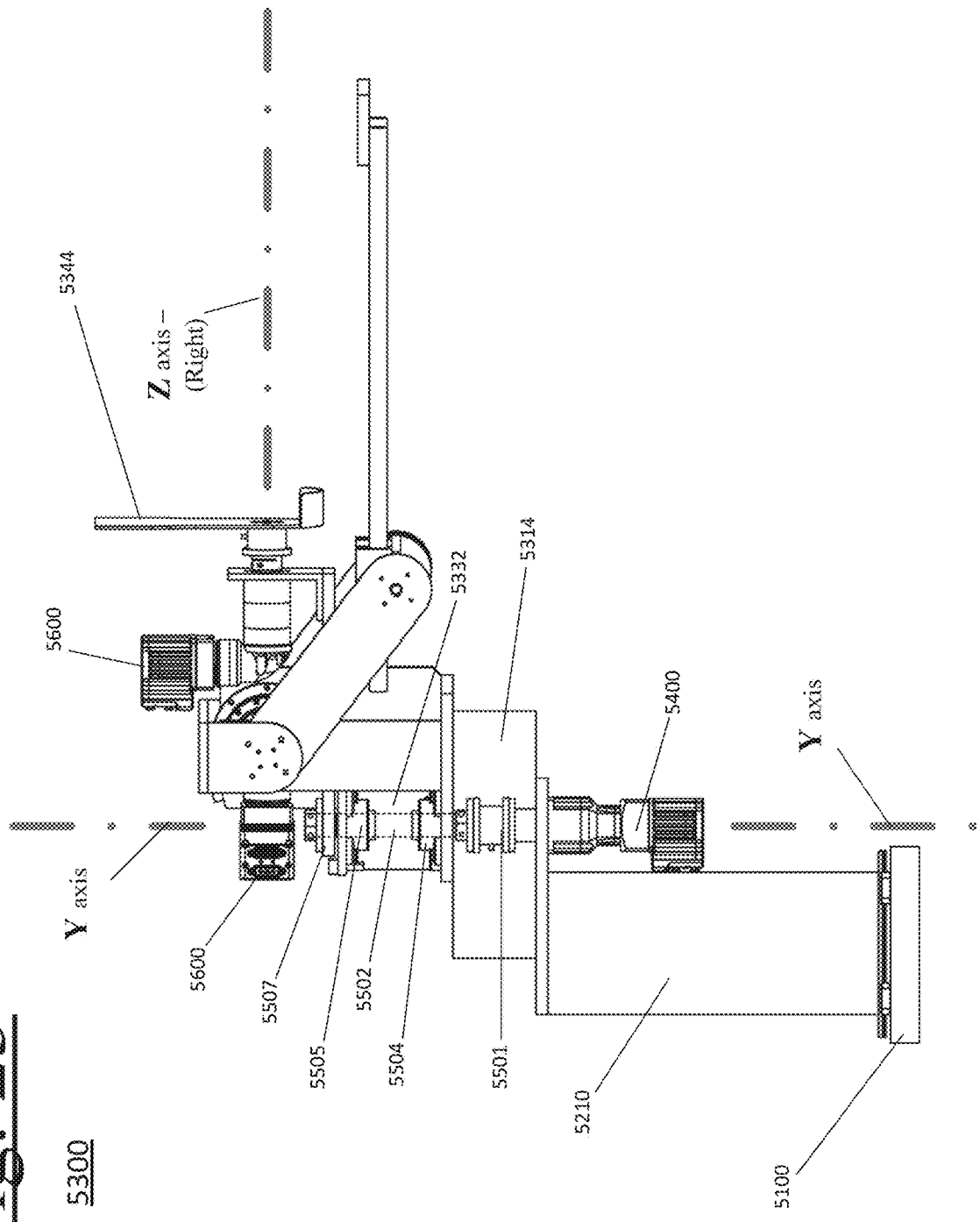

FIG. 23 is a right side elevation view of the right lower leg supporting apparatus 5300, with certain elements not shown for purposes of explanation.

Figure 24:
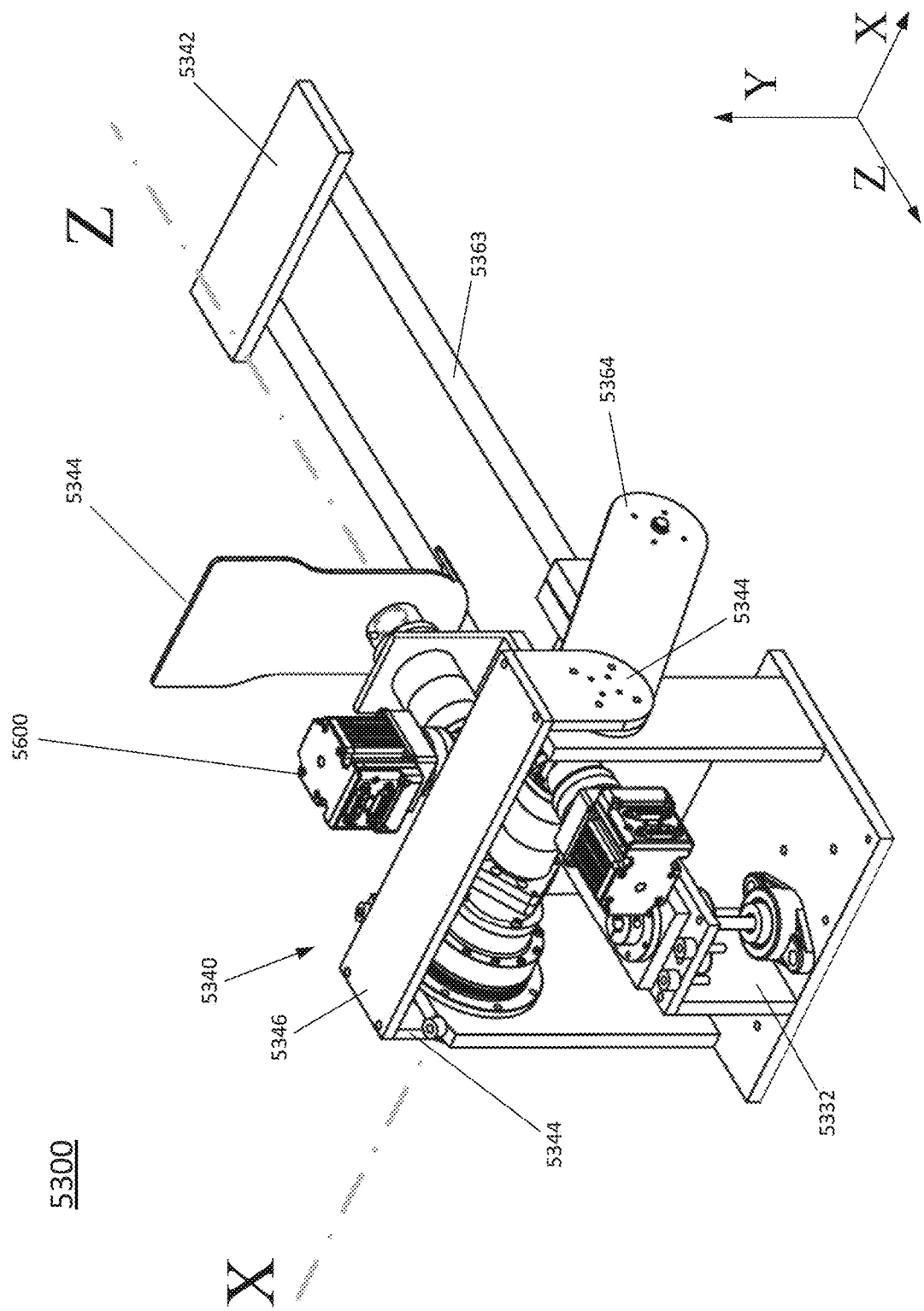

FIG. 24 is a pictorial view of a portion of the right lower leg supporting apparatus 5300 of FIG. 23, showing certain details.

Figure 25:
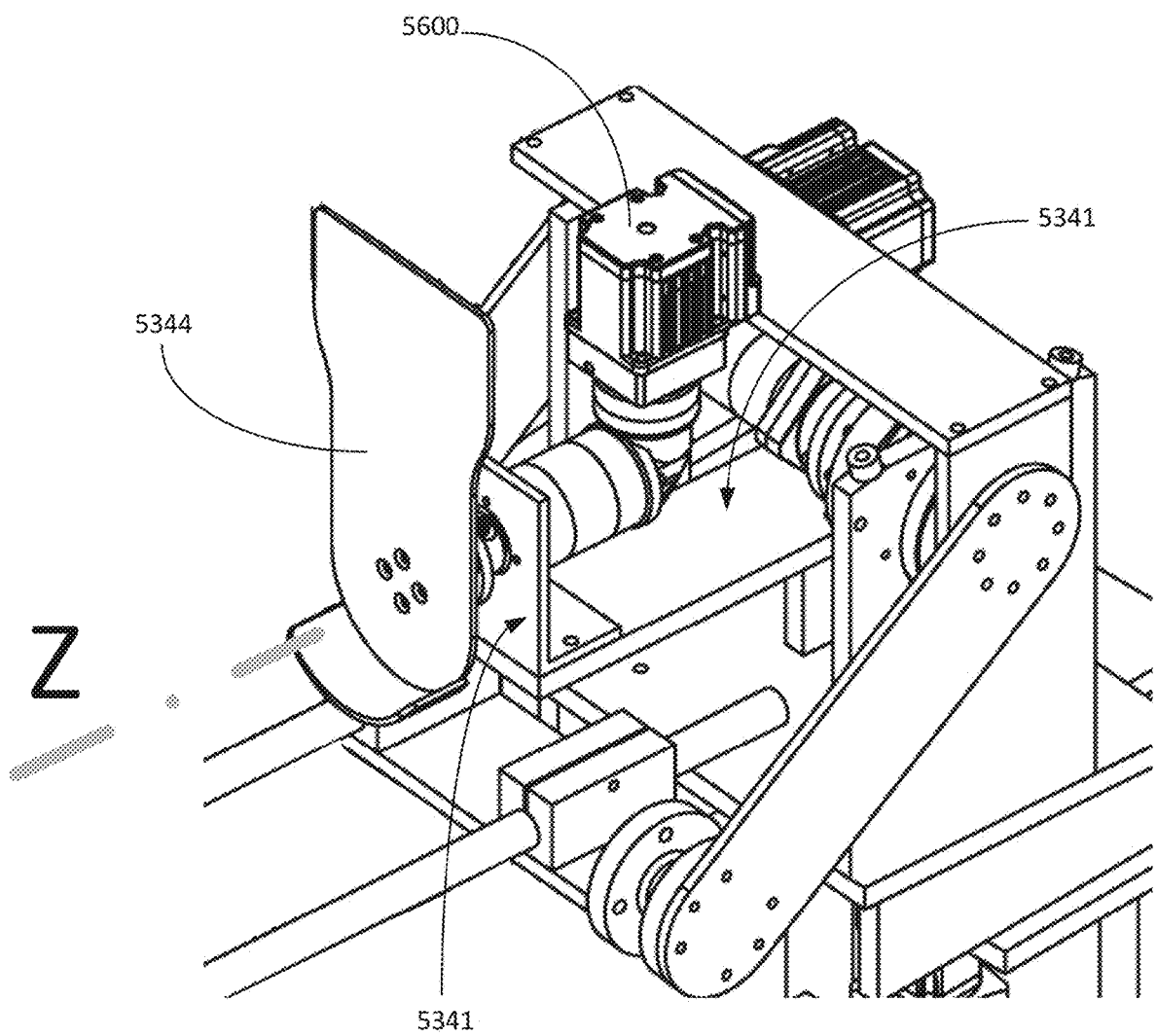

FIG. 25 is a pictorial view of a portion of the right lower leg supporting apparatus 5300, taken from the opposite side as that shown in FIG. 24.

Figure 26A:
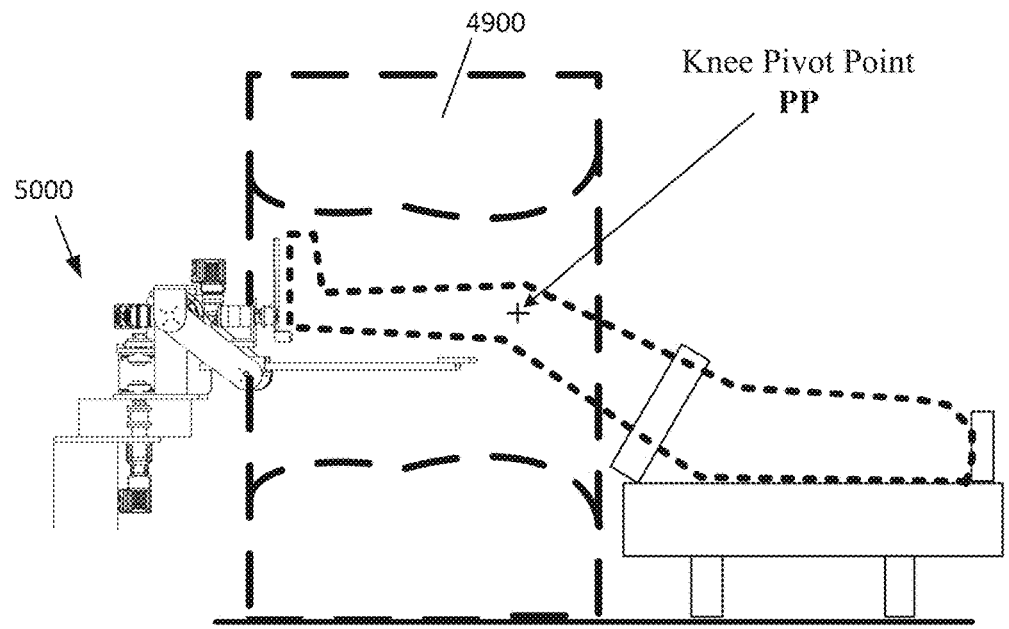
Figure 26B:
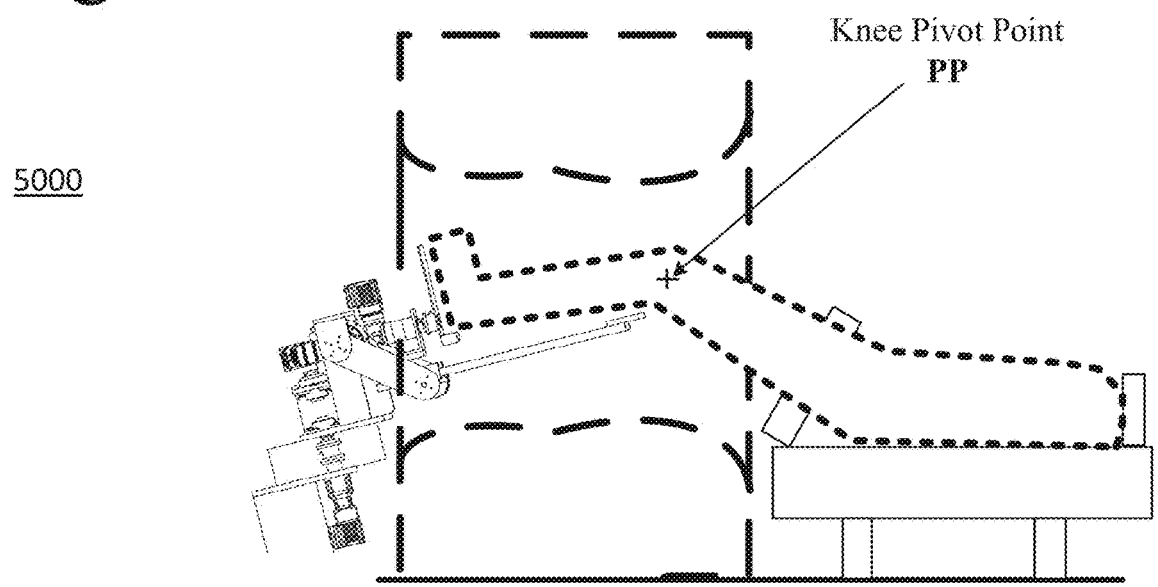

FIGS. 26A and 26B show two sequential illustrative views similar to FIG. 17, except that the leg testing apparatus 5000 is configured to be moved between the two positions shown, resulting in different flexions of the knee (Note that 26A knee is in a more extended position than the 26B knee.)

DETAILED DESCRIPTION OF VARIOUS EMBODIMENTS

Various embodiments of the present invention will now be described more fully hereinafter with reference to the accompanying drawings, in which some, but not all embodiments of the invention are shown. Indeed, embodiments of the invention may be embodied in many different forms and should not be construed as limited to the embodiments set forth herein. Rather, these embodiments are provided so that this disclosure will satisfy applicable legal requirements. Unless otherwise defined, all technical and scientific terms used herein have the same meaning as commonly known and understood by one of ordinary skill in the art to which the invention relates. The term "or" is used herein in both the alternative and conjunctive sense, unless otherwise indicated. Like numbers refer to like elements throughout.

I. ELEMENT LIST

10 Overall RKT apparatus
20 main frame assembly
30 support cushion
40 sliding support framework
50 pivoting leg support frame assemblies (2)
60 knee support/stabilizing assemblies (2)
80 thigh retention assemblies (2)
1000 tibia positioning assembly
1100 sliding frame assembly (supports Y drive assembly)
1101 sliding frame members (FIG. 7)
1102 bearings (FIG. 7)
1103 flange adaptor (FIG. 7)
1104 torque transducer (Y axis)
1110 frame cap assembly (attached to pivot plate)
1200 pivoting plate assembly (supports X/Z/yoke/calf)
1201 pivoting plate
1210 L-shaped flange brackets (2) (support X)
1211 bearing (support X)
1212 stub flange (supports yoke/calf)
1213 flange bracket (supports yoke/calf)
1220 L bracket (support Z)
1221 flange adaptor (support Z)
1222 torque transducer (Z axis)
1300 foot rotation assembly
1400 yoke assembly (FIG. 4)
1410 yoke top plate
1420 yoke end plates (2)
1430 limit plate
1500 calf bias assembly
1510 side leg members (2)
1520 plate
1530 torque transducer (X axis)
1540 stub flange
1550 bearing
1560 telescoping rod assembly
1570 calf bias plate
2000 x-axis drive assembly
2010 drive motor
2020 gear box
2030 output shaft
2100 y-axis drive assembly
2130 output shaft
2200 z-axis drive assembly
2210 drive motor
2220 gear box
2230 output shaft
3001 Spherical member (with center C1)
3002 Spherical member (with center C2)
3003 Spherical member (with center C3)
4000 Spherical cage
4900 Exemplary CT scanning device
4950 Patient body support apparatus
4951 Link
4952 Patient thigh restraints
4956 Patient back support
4959 Patient shoulder restraint
4960 Patient body
4961 Patient upper body
4962 Patient upper leg
4964 Patient Lower leg
5000 Overall Leg Testing Apparatus
5100 Lower Frame Member
5101 Slide assemblies (4 shown)
5200 Left Lower Leg Supporting Apparatus
5260 Calf bias assembly
5300 Right Lower Leg Supporting Apparatus
5400 X Drive Assembly (for AP)
5502 Vertical Shaft
5504 Lower Bearing
5505 Upper Bearing
5507 Plate-to-shaft mounting flange
5600 Z Drive Assembly (for internal and external rotation)
5300 Right Lower Leg Supporting Apparatus
5310 Lower Vertical Frame Members (2)
5312 Lower Frame Table
5314 Intermediate Vertical Frame Members (2)
5320 Intermediate Frame Table
5322 Short Upper Vertical Frame Members (2)
5330 Upper Frame Table
5332 Long Upper Vertical Frame Members (2)
5340 Pivoting Horizontal Foot Support Plate
5341 Pivoting Vertical Foot Support Flange
5344 Foot Plate 5350 Yoke Assembly
5342 yoke top plate
5344 yoke end plates (2)
5346 limit plate
5360 Calf bias assembly (Similar to calf bias assembly 1500)
5362 Calf bias plate
5363 Extendible rod assembly
5364 Side leg members (2)

II. DETAILED DESCRIPTION

Reference will now be made in detail to one or more embodiments of the present assembly, an example of which is illustrated in the accompanying drawings. The embodiments are described by way of explanation, and not by way of limitation. Indeed, embodiments of the invention may be embodied in many different forms and should not be construed as limited to the embodiments set forth herein. Rather, these embodiments are provided so that this disclosure will satisfy applicable legal requirements.

A) The Overall Apparatus 10

1. Generally

As illustrated in at least FIGS. 1-4, various embodiments of the overall RKT (Robotic Knee Testing) device 10 may include the following features:

Main Frame Assembly 20 (FIG. 2);
Support Cushion 30 (FIG. 2);
Sliding Support Framework 40 (FIG. 2);
Two (2) Pivoting Leg Support Frame Assemblies 50 (FIG. 2);
Two (2) Knee Support/Stabilizing Assemblies 60 (FIG. 2);
Two (2) Thigh Retention Assemblies 80 (FIG. 2);
Two (2) Tibia Positioning Assemblies 1000 (FIG. 2);
Sliding Frame Assembly 1100 (FIG. 3);
Pivoting Plate Assembly 1200 (FIG. 4);
Two (2) Foot Rotation Assemblies 1300 (FIG. 3);
Yoke Assembly 1400 (FIG. 3);
Calf Bias Assembly 1500 (FIG. 3);
"X"-axis Drive Assembly 2000 (FIG. 4):
"Y"-axis Drive Assembly 2100 (FIG. 4); and
"Z"-axis Drive Assembly 2200 (FIG. 4).

With particular reference to FIG. 2, it should be understood that according to various embodiments, at least certain elements of the overall RKT device 10 may be sized, shaped, and/or configured in substantially the same manner as the device described in co-owned U.S. Patent Application Publication No. 2012/0046540-A1 (also Ser. No. 13/209,380), as published on Feb. 23, 2012 and filed on Aug. 13, 2011, which is hereby incorporated by reference in its entirety. As non-limiting examples, the main frame assembly 20, the support cushion 30, the sliding support framework 40, the pivoting leg support frame assembly 50, the knee support/stabilizing assembly 60, and the thigh retention assembly 80 illustrated in at least FIG. 2 may be configured, sized, and/or shaped substantially the same as the comparable elements, as described in Ser. No. 13/209,380, which is, as previously noted, incorporated by reference in its entirety herein. Of course, certain embodiments, including those indicated hereinabove or otherwise, of the overall RKT device 10 may have one or more of these elements sized, shaped, and/or configured in a substantially different manner than that described in Ser. No. 13/209,380, as may be desirable for one or more applications.

In use, as will be described in further detail below, a patient (see FIGS. 10-11) may be positioned within the various embodiments of the overall RKT device 10, such that their knees are adjacent the knee support/stabilizing assemblies 60, their thighs are adjacent the thigh retention assemblies 80, and their feet are retained within the tibia pivoting assemblies 1000, particularly adjacent a foot plate 1300 thereof (see FIG. 4).

Movement of the lower leg of the patient may be detected by non-invasive systems utilizes sensors or markers that are attached to the skin, including but not limited to optoelectronic, ultrasonic, and electromagnetic motion analysis systems.

2. Tibia Positioning Assemblies 1000

According to various embodiments, with reference to FIG. 2, the overall RKT device 10 comprises may comprise two tibia positioning assemblies 1000, each generally configured to support and/or constrain at least one of a patient's tibia and foot so as to facilitate evaluation of movement thereof in response to the imposition of one or more forces about one or more axes (e.g., the X, Y, and/or Z axes, as described later herein). In certain embodiments, the two the tibia positioning assemblies 1000 may be substantially identical in size, shape, and configuration. In other embodiments, only a single tibia positioning assembly 1000 may be provided, for example, where only a single leg of a patient is of concern for treatment.

It should be noted, however, that according to various embodiments, at least the X-axis drive assemblies 2000 of FIG. 4 that form a portion of each tibia positioning assembly 1000 may be configured so as to be substantially mirror images of one another, even though such a configuration is not expressly illustrated in FIG. 2. Instead, in the illustrated embodiment of FIG. 2, the "X" axis drive assemblies 2000 (see again FIG. 4) are not substantially mirror images of one another, as may be desirable for certain applications. In those embodiments involving mirror image positioned X axis drive assemblies 2000, however, it should be understood that when certain movements (e.g., anterior-posterior, varus-valgus, internal-external rotation, etc.) are imposed upon the patient's limb during operation, the same movement and in particular the same orientation of movement will be imposed upon both limbs. As a non-limiting example, when anterior movement is imposed upon a patient's first tibia via rotation of one of the drive assemblies, the same activation signal will likewise impose anterior movement upon the patient's second tibia in those embodiments having the X axis drive assemblies positioned as substantial mirror images relative to one another. In contrast, in those other embodiments, as may be desirable for particular applications, where the tibia positioning assemblies 1000 may not be "mirror-imaged" relative to one another, a single activation signal would impose anterior movement upon one tibia and posterior movement upon the other (or varus upon one and valgus upon the other, or internal rotation upon one and external rotation upon the other, etc.). This should be understood with reference to at least FIGS. 2 and 4 in concert with one another.

With that in mind and turning now to FIGS. 3 and 4 in combination, various embodiments of each tibia positioning assembly 1000 (isolated for purposes of a concise and clear disclosure) generally comprise a sliding frame assembly 1100, a pivoting plate assembly 1200, a foot rotation assembly 1300, a yoke assembly 1400, a calf bias assembly 1500, a X-axis drive assembly 2000, a Y-axis drive assembly 2100, and a Z axis drive assembly 2200. These assemblies will now be described, in turn, below.

3. Sliding Frame Assembly 1100

According to various embodiments, each tibia positioning assembly 1000 comprises a sliding frame assembly 1100 that provides an interface between at least the Y-axis drive assembly 2100 and the main frame assembly 20 of the RKT device 10. As may be seen from FIG. 2, the sliding frame assembly 1100 is, in certain embodiments, linearly slidable along the pivoting leg support frame assembly 50, so as to accommodate varying lengths of patient legs. In at least one embodiment, the sliding frame assembly 1100 may be configured for translational movement relative to the pivoting leg support frame assembly 50 and/or the main frame assembly 20 of the RKT device 10 in a manner substantially the same as the sliding frame 120 described in Ser. No. 13/209,380, as incorporated by reference herein and as may be desirable for one or more applications.

Turning for a moment to FIG. 7, it may be seen that the sliding frame assembly 1100 generally comprises a plurality of sliding frame members 1101, each configured to form a platform for substantially supporting a first (e.g., lower positioned) portion of the Y-axis drive assembly 2100. In certain embodiments, the sliding frame assembly 1100 comprises a pair of bearings 1102 and a flange adaptor 1103 configured to attach a second (e.g., higher positioned) portion of the Y-axis drive assembly 2100 relative to the pivoting plate assembly 1200, as will be described in further detail below. A torque transducer 1104 may also be provided to evaluate the torque along the drive line between an output shaft 2130 of the Y-axis drive assembly 2100 and a pivoting plate 1201, all as will be described in further detail below. In these and still other embodiments, the sliding frame assembly 1100 may further comprise a frame cap assembly 1110, which incorporates a plurality of members (shown, but not numbered) that cover (and thus protect) the second portion of the Y-axis drive assembly 2100.

Remaining with FIG. 7 and also with reference to FIGS. 5-6, it should be understood that the sliding frame assembly 1100, beyond being configured to permit selectable translational movement thereof relative to the main frame assembly 20 of the RKT device 10, is configured to support the Y-axis drive assembly 2100 such that a longitudinal axis thereof lies substantially along the Y-axis (see in particular FIGS. 5 and 6). In this manner, during operation of the RKT device 10, activation of the Y-axis drive assembly 2100 provides rotation about the Y-axis. As should be understood from FIGS. 1-4 generally, such rotation about the Y-axis, as has been previously mentioned, may in turn be configured to impose varus-valgus movement upon an associated positioned patient's leg.

It should also be noted, with reference to FIGS. 4-5 and 7, and as will be described in further detail below in the context of operation of the RKT device 10, the pair of bearings 1102 and the flange adaptor 1103, which operatively connect the Y-axis drive assembly 2100 and the sliding frame assembly 1100 relative to the pivoting plate assembly 1200 are configured such that rotation about the Y-axis results in corresponding movement of the foot plate 1300 and thus the patient's foot and/or tibia about the same. Such movements, imposed as the result of operation will, however, be described in further detail elsewhere herein.

4. Pivoting Plate Assembly 1200

Returning now with particular emphasis upon FIG. 4, the pivoting plate assembly 1200 of the tibia positioning assembly 1000 is illustrated. The pivoting plate assembly 1200 according to various embodiments comprises a pivoting plate 1201, which is mounted relative to the sliding frame members 1101 of the sliding frame assembly 1100 (see, e.g., FIG. 7). In certain embodiments, as illustrated in FIG. 4, the pivoting plate 1201 is mounted to the frame cap assembly 1110 (see again FIG. 7), so as to also provide a platform for supporting the X-axis and Z-axis drive assemblies 2000, 2200, the configuration of which as will be described elsewhere herein.

In various embodiments, as mentioned, the pivoting plate assembly 1200 comprises a pivoting plate 1201 that is mounted to the frame cap assembly 1110. In this manner, the mounting of the pivoting plate 1201 relative to the frame cap assembly 1110 serves to fixedly couple movement of the pivot plate 1201 to movement imposed by the Y-axis drive assembly 2100 about the Y-axis.

The pivoting plate assembly 1200 according to various embodiments further comprises a pair of L-shaped flange brackets 1210 (see FIG. 4), each configured to be mounted on opposing ends of the pivoting plate 1201, such that the X-axis drive assembly 2000 may be mounted there-between. In certain embodiments, as may be seen in FIG. 4, each of the L-shaped flange brackets 1210 may comprise an opening configured to receive at least a portion of the X-axis drive assembly 2000. In at least the illustrated embodiment, the pivoting plate assembly 1200 further comprises a bearing 1211 and a stub flange 1212, each of which are mounted adjacent the second of the two L-shaped flange brackets 1210, namely further adjacent the drive motor 2010 of the X-axis drive assembly 2000. A flange bracket 1213 is similarly attached adjacent the first of the two L-shaped brackets 1210, namely substantially adjacent the gear box 2020 of the X-axis drive assembly 2000. In this manner, the L-shaped flange brackets 1210 provide stable support for the X-axis drive assembly 2000.

With continued reference to FIG. 4, it should be understood that the configuration of the previously described components of the pivoting plate assembly 1200 relative to the X-axis drive assembly 2000 are configured such that rotation of the X-axis drive assembly substantially about the X axis (see FIG. 5) translates into rotational movement of the yoke assembly 1400 and the calf bias assembly 1500, both as will be described in further detail below. Such movement is imparted due, at least in part, to the further mounting of the flange bracket 1213 and the stub flange 1212 of the pivoting plate assembly 1200 to opposing ones of a pair of side leg members 1510 of the yoke assembly 1500, again, as will be detailed further below.

Beyond the above-described components of the pivoting plate assembly 1200 configured to support and/or translate movement imposed by the X-axis drive assembly 2000, the plate assembly 1200 further comprises according to various embodiments certain components configured to support the Z-axis drive assembly 2200. In particular, with continued reference to FIG. 4, it may be seen that the pivoting plate assembly 1200 in certain embodiments further comprises an L bracket 1220, a flange adaptor 1221, and a torque transducer 1222, all oriented relative to and along the Z-axis.

The L bracket 1220 according to various embodiments is mounted to the pivoting plate 1201 such that it is oriented substantially perpendicular relative to the pair of L-shaped flange brackets 1210 described previously herein as being configured for supporting the X-axis drive assembly 2000. In this manner, as illustrated further in FIGS. 5-6, it should be understood that the X-axis drive assembly 2000 and the Z-axis drive assembly 2200 are likewise positioned substantially perpendicular relative to one another, so as to provide respective rotation about the likewise mutually perpendicular X and Z axes.

The flange adaptor 1221 and the torque transducer 1222 are likewise mounted to the L bracket 1220 and the foot plate 1300 (described elsewhere herein), such that rotational movement of the Z-axis drive assembly 2200 is converted into a rotational force about the Z-axis that is not only measured by the torque transducer 1222 (e.g., to ensure an appropriate or desired force is supplied/imposed) but also transferred onto the foot plate 1300, resulting in corresponding rotational movement thereof about the Z-axis. Notably, as will be described further below, the rotational movement of the foot plate 1300 about the Z-axis is configured to provide internal and/or external rotation a patient's tibia during operational testing performed according to various embodiments.

5. Foot Rotation Assembly 1300

According to various embodiments, as may be understood from at least FIGS. 3-4 and 7, the foot plate assembly 1300 of each of the tibia positioning assemblies 1000 may be pivotably mounted relative to the pivoting plate assembly 1200 of the (linearly) sliding frame assembly 1100 via the Z-axis drive assembly 2200, as will be described in further detail below. In certain embodiments, the foot plate assembly 1300 is configured to rotate about the Z axis in response to rotation of (e.g., to) an output shaft 2230 of the Z axis drive assembly 2200 (see also FIG. 7), as will also be described in further detail below. In these and still other embodiments, with reference also to FIG. 4, the foot plate assembly 1300 is mounted in series to the torque transducer 1222, the flange adapter 1221, and the L bracket 1220 of the pivoting plate assembly 1200.

With reference again to FIG. 3 and also to FIG. 10, it should be understood that rotation of the foot plate assembly 1300 about the Z axis, as imposed by the Z-axis drive assembly 2200 is configured to provide movement for tibia internal and external rotation testing. Details of the drive assembly 2200 will be described in further detail below in the context of operational parameters of the RKT device 10.

It should also be understood, however, that rotation of the pivoting plate assembly 1200 about the Y axis, via the "Y" Axis drive assembly will also impose movement upon the foot plate 1300, namely via its fixed mounting relative to at least the pivoting plate assembly about the "Y" axis. In other words, in certain embodiments, although the foot plate 1300 may be configured to rotate about the Z axis, it may also be configured to move (e.g., to swivel) in response to rotation of the pivoting plate assembly 1200 about the Y axis, all as will be described in further detail below.

6. Yoke Assembly 1400

Returning to FIGS. 3-4 and 7, various embodiments of the tibia positioning assembly 1000 further comprise a yoke assembly 1400. In certain embodiments, the yoke assembly 1400 comprises a yoke top plate 1410, a pair of yoke end plates 1420, and at least one limit plate 1430. Each of these components may be seen, in particular, in the exploded view of FIG. 4.

Indeed, with particular reference to FIG. 4, the yoke end plates 1420 are generally configured according to various embodiments to operatively mount, respectively, to the flange bracket 1213 and the stub flange 1212 of the pivoting plate assembly 1200, as such components have been previously described herein. In certain embodiments, respective side leg members 1510 of a calf bias assembly 1500, as will be described below, may be positioned intermediate the yoke end plates 1420 and the respective flange bracket 1213 and stub flange 1212. In this manner, as will be described in further detail below, rotational forces imposed by rotational movement of the X-axis drive assembly 2000 about the X-axis may be transferred from the drive assembly 2000 and onto both the side leg members 1510 of the calf bias assembly 1500 and the yoke end plates 1420 of the yoke assembly 1400.

Remaining with FIG. 4 and also with reference to FIG. 5, it may be seen that the yoke top plate 1410 is, according to various embodiments, positioned so as to extend substantially between the respective yoke end plates 1410. In this manner, as rotational movement of the X-axis drive assembly 2000 transfers rotational movement onto the yoke end plates 1420, the latter further transfers the same rotational movement onto the yoke top plate 1410. In certain embodiments, the limit plate 1430 of the yoke assembly 1400 may be further configured with at least two rubber stops that are positioned so as to contact opposing sides of the yoke top plate 1410 and thus define a "limited" range of motion thereof, in response to rotational movement imposed by the X-axis drive assembly 2000. In this manner, a degree of movement and/or force and/or torque that may be imposed upon a patient's limb may be restricted for joint protection and/or patient comfort Still further, it should be appreciated that the yoke assembly 1400, and in particular, the yoke end plates 1420 are further configured to transfer rotational movement imposed by the X-axis drive assembly 2000 onto at least the side leg members 1510 of the calf bias assembly 1500, as described immediately below. Of course, in certain embodiments, it should be appreciated that it is the flange bracket 1213 and the stub flange 1212 of the pivot plate assembly 1200 and their respectively fixed mounts to each of the yoke end plates 1420 and the side leg members 1510 that transfers the rotational movement thereupon. In other embodiments, the yoke assembly 1400 may be otherwise configured, as may be desirable for particular applications.

Returning for a moment to FIG. 4, with reference also to FIGS. 10-11, it should be appreciated that the above-described transference of rotational force (and thus movement) from the X-axis drive assembly 2000 is configured such that the RKT device 10 may pivot, as illustrated, along the X-axis, so as to move a patient's tibia from the illustrated position of FIG. 10 to that of FIG. 11 (and vice versa). Of course, such rotation involves not only rotational movement of the yoke assembly 1400 about the X-axis, but also the same by the calf bias assembly 1500, which will now be described immediately below. As also described in further detail below, in certain embodiments, such movement may impose rotational movement of the patient's limb, whether about the same X-axis or about a secondary and parallel X-axis, as may be seen in at least FIG. 10. These and other features, as may be appreciated better with consideration to relative movements imposed during operation of the RKT device will be described in further detail below.

7. Calf Bias Assembly 1500

According to various embodiments, returning again to FIG. 4, the tibia positioning assembly 1000 further comprises a calf bias assembly 1500, which may itself comprise a pair of side leg members 1510, a cross plate 1520, a torque transducer 1530, a stub flange 1540, a bearing 1550, a telescoping rod assembly 1560, and a calf bias plate 1570.

With continued reference to FIG. 4, the pair of side leg members 1510 are, according to various embodiments, fixedly attached at a first end thereof to the flange bracket 1213 and the stub flange 1212 of the pivoting plate assembly 1200, which also supports at least the X-axis drive assembly 2000 and the yoke assembly 1400. In this manner (i.e., via this connection/attachment), the calf bias assembly 1500 is likewise supported by the pivoting plate assembly 1200 according to various embodiments.

Opposing ends of the side leg members 1510 are configured according to various embodiments to mate with either a stub flange 1540/bearing 1550 pairing or a torque transducer 1530. Such is configured substantially the same as the torque transducer 1222 and the bearing 1211/stub flange 1212 pairing previously described herein. In other words, the torque transducer 1530 is configured to measure and transfer a force imposed upon the side leg members 1510 by the X axis drive assembly 2000 onto at least the plate 1520 and/or the calf bias plate 1570 of the calf bias assembly 1500.

Returning to FIG. 4, a plate 1520 and a telescoping rod assembly 1560 are also provided and configured to fixedly link the torque transducer 1530 to the calf bias plate 1570. With reference to FIGS. 10-11, and as will be described in further detail below, this configuration facilitates transfer of the rotational force (and thus torque) imposed upon the yoke assembly 1400 by the X-axis drive assembly 2000 onto not only the calf bias assembly 1500, but also the patient's tibia positioned substantially adjacent to the calf bias plate 1570. Indeed, as should be understood from these figures, imposing a force in the clockwise direction (relative to FIGS. 10-11, in particular) results in a substantially "upward" movement of the tibia, further accompanied by rotation about the illustrated tibia pivot point. In this manner, as will be described in further detail, activation of the X axis drive assembly results in forces being applied to the tibia substantially along the Y axis in the anterior and/or posterior direction relative to the tibia.

Although reference has been made herein to a telescoping rod assembly 1560, which should be understood to be extendable in length (e.g., between the calf bias plate 1570 and the plate 1520 adjacent the pivoting plate assembly 1200, certain embodiments may have otherwise configured assemblies 1560, provided such are capable of accommodating differing lengths of patient's legs positioned adjacent thereto. In still other embodiments, the rod assembly 1560 may even not be adjustable, in a telescoping fashion or otherwise, as may be desirable for particular applications.

8. "X"-Axis Drive Assembly 2000

Remaining with FIG. 4, the X-axis drive assembly 2000 is illustrated, as configured such that a longitudinal axis thereof lies substantially along the further illustrated X-axis, as also defined in at least FIG. 5. With reference to FIGS. 7 and 12, it should be understood that various embodiments of the X-axis drive assembly 2000 comprise a drive motor 2010, a gear box 2020, and an output shaft 2030 operatively coupled to the gear box.

In certain embodiments, the drive motor 2010 may comprise a servomotor configured to provide a rotational force, although still other embodiments may include alternative mechanical or even manual methods of force generation and application, as may be desirable for particular applications and as commonly known and understood in the art. Of course, it should be understood that any of a variety of alternative configurations may be envisioned as within the scope of the present invention, as may be desirable for a given application.

In certain embodiments, the drive motor 2010, however particularly configured, may be at least configured with a housing mounted relative to the pivoting plate assembly 1200, such that the drive motor drives the corresponding output shaft 2030, which itself drives at least the yoke assembly 1400 and the calf bias assembly 1500 based upon the structural relationships previously described herein. In this manner, according to various embodiments, the X-axis drive assembly 2000 is configured to facilitate rotation of at least a portion of the RKT device 10 about the X-axis (see FIG. 5), such that a user of the device may evaluate "AP" (anterior-posterior) movement of the tibia with respect to the femur at the knee about an X-axis of rotation distal to the foot.

9. "Y"-Axis Drive Assembly 2100

Turning now with particular reference to FIG. 7, the Y-axis drive assembly 2100 is illustrated, as may be configured according to various embodiments such that a longitudinal axis thereof lies substantially along the Y-axis, the latter of which as is defined in at least FIG. 5. With reference to FIG. 12, it should be understood that various embodiments of the Y-axis drive assembly 2100 comprise a drive motor 2110, a gear box 2120, and an output shaft 2130 operatively coupled to the gear box.

In certain embodiments, the drive motor 2110 may comprise a servomotor configured to provide a rotational force, although still other embodiments may include alternative mechanical or even manual methods of force generation and application, as may be desirable for particular applications and as commonly known and understood in the art. Of course, it should be understood that any of a variety of alternative configurations may be envisioned as within the scope of the present invention, as may be desirable for a given application.

In certain embodiments, the drive motor 2110, however particularly configured, may be at least configured with a housing mounted relative to the pivoting plate assembly 1200, such that the drive motor drives the corresponding output shaft 2130, which itself imposes rotation upon at least the pivoting plate assembly 1200 and the foot plate assembly 1300 based upon the structural relationships previously described herein. In this manner, according to various embodiments, the Y-axis drive assembly 2100 is configured to facilitate rotation of the foot plate assembly 1300 about the Y-axis (see FIG. 6), such that a user of the device may evaluate varus-valgus conditions about a Y-axis of rotation distal to the foot.

10. "Z"-Axis Drive Assembly 2200

Returning again to FIGS. 4 and 12, the Z-axis drive assembly 2200 is illustrated according to various embodiments, as may be configured such that a longitudinal axis thereof lies substantially along the Z-axis, the latter of which as is defined in at least FIG. 5. With reference to FIG. 12, it should be understood that various embodiments of the Z-axis drive assembly 2200 comprise a drive motor 2210, a gear box 2220, and an output shaft 2230 operatively coupled to the gear box.

In certain embodiments, the drive motor 2210 may comprise a servomotor configured to provide a rotational force, although still other embodiments may include alternative mechanical or even manual methods of force generation and application, as may be desirable for particular applications and as commonly known and understood in the art. Of course, it should be understood that any of a variety of alternative configurations may be envisioned as within the scope of the present invention, as may be desirable for a given application.

In certain embodiments, the drive motor 2210, however particularly configured, may be at least configured with a housing mounted relative to the foot plate assembly 1300 based upon the structural relationships previously described herein. In this manner, according to various embodiments, the Z-axis drive assembly 2200 is configured to facilitate rotation of the foot plate assembly 1300 about the Z-axis (see FIG. 6), such that a user of the device may evaluate (internal-external) movement about a Z-axis of rotation.

It should further be understood that any of the X-, Y-, or Z-axis drive assemblies 2000-2200 may be structurally configured substantially the same relative to one another, with the only substantive difference being the relative axis of rotation about which each is oriented. Of course, it should also be understood that any of a variety of alternative configurations may be envisioned as within the scope of the present invention, as may be desirable for a given application.

It should also be understood that although in certain embodiments, the X-, Y-, and/or Z-axis drive assemblies 2000-2200 may be oriented such that at least two thereof are mutually orthogonal and intersecting relative to one another, in other embodiments, one or more of the drive assemblies 2000-2200 may be offset relative to the remainder of the drive assemblies, such that non-intersecting, although orthogonal axes are defined. This feature and further variations thereof are described in further detail elsewhere herein, and may be understood generally with reference to at least FIG. 7 (showing how the Y and X axis may be offset relative to one another, as along a longitudinal axis of the RKT device in its entirety); FIGS. 8 and 9 (showing the same relative offset between the X and Y axes, when viewed in combination); and FIGS. 13-15 (as will be described elsewhere herein).

B) Overall Operation

Each of the various above-described features and their use will now be described in further detail herein-below.

1. Generally

Three drive assemblies are used, namely a "X" axis drive assembly 2000, a "Y" axis drive assembly 2100, and a "Z" axis drive assembly 2200. Each drive assembly can be understood to include, in various embodiments, a mounting frame, a drive motor and a gearbox having an output shaft, as all previously described herein. By operation of any of the drive motors, rotational movement is provided to a corresponding output shaft with intermediate reduction (or expansion) gearing as needed to provide adequate torque and rotational speed.

According to various embodiments, torque sensors are provided in the power line in order to provide torque readings as known in the art relating to each of these three drive assemblies. These torque readings may be calibrated and calculated as needed to correspond to known torque or force values imparted to a patient's limb(s).

As noted elsewhere, movement of the patient's body parts may be detected by non-invasive systems utilizes sensors or markers that are attached to the skin, including but not limited to vision, optoelectronic, ultrasonic, and electromagnetic motion analysis systems.

The three drive assemblies are configured about mutually perpendicular X-, Y-, and Z-axes of rotation, as illustrated in at least FIG. 5. As such, the respective forces (and corresponding torque) imposed by the drive assemblies are configured to selectively evaluate "AP" (anterior-posterior) movement of the tibia with respect to the femur at the knee about the X-axis of rotation distal to the foot, varus-valgus conditions about the Y-axis of rotation distal to the foot, and "IE" (internal-external) movement about the Z-axis of rotation. Similarly, motions can be defined in such a way as to be relative to a co-ordinate system defined by the tibia as opposed to the femur.

According to various embodiments, the patella is clamped in place for all three types of testing procedures. In these and still other embodiments, a strap (not illustrated) may be coupled with the calf bias plate of assembly 1500 for use only during AP testing. Such a strap/plate or cage or box assembly may be configured as commonly known and understood in the art so as to provide selective restraint of the user's limb (e.g., as a non-limiting example, the strap may be operatively connected to one or the other sides of the calf bias plate 1570 and selectively attachable (e.g., via Velcro or the like) on the opposing side, with the strap also being in certain embodiments, selectively adjustable, as may be desirable). The strap/plate, cage or box assembly could be situated such that all sides are in constant contact with the calf or it could be configured such that there is space between the strap/plate, cage or box assembly and the calf. When there is space the assembly will move for a small distance before it contacts the calf and applies appropriate forces.

2. X-Axis Drive Operation due to Component Relationships

Movement about the X axis is configured to provide "AP" (anterior-posterior) movement of the tibia, due to forces up or down on the tibia as the foot is maintained in a stationary position by the foot plate assembly 1300. In particular, the tibia pivots about an X oriented axis passing through the ankle—note this is a different X axis (albeit parallel) to the X axis "of the machine", aka the "machine X axis," all of which may be understood with reference to FIG. 11.

With reference to FIG. 4, according to various embodiments, the X drive assembly 2000 has its frame attached to the first of the two L-shaped flange brackets 1210, which is itself attached to the pivoting plate 1201. The output shaft of the X drive assembly goes through the hole in the L-shaped flange bracket (1st of 2), which in certain embodiments has a larger hole than its sister L-shaped bracket ($2^{nd}$ of 2). The output shaft of the X drive assembly drives a flange bracket 1213, which drives one end of a side leg member 1510 of the calf bias assembly 1500, as previously described herein. A yoke end plate 1420 and the flange bracket 1213 sandwich the end of the side leg member, such that relative movement is transferred there-between during operation.

The yoke end plate 1420 is part of a rigid yoke assembly 1400 that includes a yoke top plate 1410 and two yoke end plates 1420. Notably, during operation according to various embodiments, as the $1^{st}$ of the two yoke end plates rotate about the X axis so does the entire yoke assembly 1400. The $2^{nd}$ yoke end plate 1420 is attached to the upper one end of a $2^{nd}$ of two side leg members 1510 of the calf bias assembly 1500, with that end also being attached to a stub flange 1212 that is pivotably mounted relative to the $2^{nd}$ of two flange brackets. The bearing 1211 supporting the stub flange 1212 does not interact with the X axis drive assembly 2000, such that the X axis drive assembly is thus solely supported by the $1^{st}$ of two flange brackets 1210, as attached to the pivoting plate 1201.

As previously described herein, the lower end of the $1^{st}$ of two side leg members 1510 is attached to a spool-shaped torque transducer 1530, which is itself attached to a plate 1520 which supports a telescoping rod assembly 1560 that supports a calf bias plate 1570.

The lower end of the $2^{nd}$ of 2 side leg members 1510 has a bearing 1550 attached thereto, which supports stub flange 1540. This stub flange 1540 is attached to the end of the plate 1520 opposite the spool-shaped torque transducer.

In this manner, upon activation of the X-axis drive assembly, any rotational force generated by the drive thereof is transferred to the associated gear box 2020 and output shaft 2030, the latter of which rotates the flange bracket 1213. Rotation of the flange bracket 1213 causes rotation of the side leg member 1510 of the calf bias assembly 1500, which is operatively coupled to the calf bias plate 1570 via at least a telescoping rod assembly 1560, which may include one or more telescoping rods configured to accommodate varying patient limb lengths.

The resulting movement imposed upon the calf bias plate 1570 is further illustrated in FIGS. 10-11, wherein pre- and post-movement positions are respectively shown. As may be further understood from these figures, rotation occurs not only about the X-axis about which the X drive assembly 2000, but also about a tibia pivot point about a stationary constrained ankle, as restrained in the foot rotation assembly 1300. In this manner, a user of the device may selectively evaluate "AP" (anterior-posterior) movement of the tibia with respect to the femur at the knee about an X-axis of rotation distal to the foot. In certain embodiments, such selective evaluation involves selective locking of the one or more of the remaining Y- and Z-axis drive assemblies, upon activation of the X-axis drive assembly 2000. This selective locking can result in the foot remaining still while the x-axis motor rotates about the X-axis distal to the foot resulting in the calf being manipulated in the anterior-posterior direction representing Y-axis translation.

3. Y-Axis Drive Operation due to Component Relationships

The Y-Axis drive assembly 2100 is configured according to various embodiments to rotate the foot plate about the Y axis relative to the sliding frame assembly 1100, so as to evaluate varus-valgus conditions. The strap associated with the calf support member is not used. However the patella is clamped in place, as previously described herein.

As described previously herein with reference to FIG. 7, the frame of the Y axis drive assembly 2100 is attached to the underside of the pivoting plate 1201 (see also FIG. 4), and includes an output shaft 2130 that extends upwardly through a hole in the pivot plate. This output shaft 2130 attaches to a flange adaptor 1103 that attaches to a Y torque transducer 1104, which in turn attaches to a frame cap assembly 1110, which attaches to the pivoting plate 1201, all as also previously described herein. The torque transducer 1104 thus evaluates the torque along the drive line between the output shaft 2130 and the pivoting plate 1201.

With continued reference to FIGS. 4 and 7, it may be understood that because the output shaft 2130 of the Y-axis drive assembly 2100 and the foot plate 1300 are both fixedly attached to the pivoting plate (e.g., the latter via the L bracket 1220, as previously described herein), rotation transferred from the Y-axis drive assembly 2100 onto the pivoting plate 1201, resulting in it pivoting about the Y axis, is thus transferred further onto the foot plate 1300, also causing it to move about the Y axis. Notably, when such occurs without concurrent rotational transfer from the Z-axis drive assembly 2100, movement of the foot plate 1300 will thus be isolated to about the Y axis, with no rotation occurring about the Z-axis.

During operation, such isolated rotation about the Y axis facilitates evaluation of varus-valgus conditions about the Y-axis of rotation, as previously described herein. Note that rotation of about the Y-axis distal to the foot causes the foot to move in an X-axis translation which results in a Y-axis rotation about the knee. It is this Y-axis rotation at the knee that is the varus-valgus rotation. Note that the distance from the footplate to the motor determines how far the footplate will translate along the X-axis. The more the footplate translates along the X-axis the more varus-valgus movement is effected at the knee. Furthermore, the Y-axis motor may be position such that it moves the footplate but that the X-axis motor and/or the Z-axis motor are not moved during the process.

4. Z-Axis Drive Components and Operation

The Z-Axis drive assembly is configured to rotate the foot plate about the Z axis relative to the sliding frame member, so as to evaluate "IE" (internal-external) rotational movement of the patient's tibia and/or limb. The strap associated with the calf support member is not used.

With reference to FIG. 4, the foot plate 1300 is attached to a torque transducer "IE" (internal-external) movement 1222 which is attached to a flange adaptor 1221 which is attached to the output shaft 2330 (see FIG. 12) of the Z-Axis drive assembly 2300. The frame of the Z-Axis drive assembly is attached to an L Bracket 1220 which is fixedly attached to the pivot plate 1201, as described elsewhere. Also as described elsewhere, the pivot plate 1201 is attached relative to the linearly sliding frame assembly 1100 about a pivoting axis Y. However, if the Y-Axis drive assembly is not in use and is selectively locked (which it is capable of, as are the other two), then the pivot plate 1201 is likewise substantially rigidly attached relative to the sliding frame assembly 1200.

In this manner, upon activation of the Z-axis drive assembly 2200, a rotational movement and accompanying torque are transferred via the output shaft 2330 directly to the foot plate 1300, thereby providing resulting rotation of the foot plate about the Z-axis. Such permits users to, amongst other things, evaluate "IE" (internal-external) rotational movement of the patient's tibia and/or limb.

5. Right Versus Left Oriented Tibia Positioning Assemblies 1000

Although it has been previously described herein with reference to FIG. 2, it should be again noted that although only one tibia positioning assembly 1000 has been described herein, various embodiments of the overall RKT device 10 comprise two such assemblies 1000. In certain embodiments, the two assemblies are symmetrical mirror images of one another, about a center-line axis of the device 10 as a whole. In this manner, it should be understood that, as a non-limiting example, if the same activation signal is sent to each of the X-axis drive assemblies 2000, the resulting movement of each will result in anterior movement of both of the user's tibias. Consider the alternative, in the absence of a symmetrical mirror image configuration, in which instance such a signal would result in anterior movement of one tibia and posterior movement of the other. Although such a nonsymmetrical configuration may be desirable in at least one embodiment, it should be understood that according to certain embodiments described herein, the assemblies 1000 should be understood to be substantially symmetrically configured.

Still further, it should be understood that although the previous description has focused upon a single tibia positioning assembly 1000, both of the assemblies of the overall RKT device 10 are according to certain embodiments configured, sized, and shaped in substantially the same manner. Of course, it should also be appreciated that in still other embodiments, it may be desirable to have substantially differently sized, shaped, and/or configured tibia positioning assemblies 1000, such as the non-limiting example whereby at least one of the two assemblies substantially corresponds to the tibia positioning assembly described in Ser. No. 13/209,380, as has been incorporated by reference herein in its entirety.

6. Drive Assembly Decoupling

It should be understood that any drive assembly configuration 2000-2200 may be according to various embodiments decoupled from any of the other two. In fact, each of the three drive configurations could be decoupled from each of the other two so that substantially independent rotation about the respective axes thereof may be provided and thus imposed upon the patient's limb, as may be desirable for particular applications. In still other embodiments, it should be understood that two or more, and even all three drive assemblies 2000-2200 may be mutually coupled relative to one another such that movements are substantially simultaneously imposed upon the patient's limb during operation of the overall RKT device. That being said, it is often advantageous to isolate each respective movement; thus isolation (i.e., decoupling) of the movements of each of the respective drive assemblies 2000-2200 may be likewise desirable for particular applications as have been described elsewhere herein.

C) Additional Configurations
1. Spherical Configurations

Spherical configurations can be also be used to provide manipulation of the lower leg of a patient about the centers of the spheres.

FIG. 13 is an alternate configuration showing the use of spherical elements 3001, 3002 for manipulating the lower leg of a patient (shown in dotted line) about the centers of the spheres.

Sphere 3001 is driven by the exemplary roller and drive assembly (which can include two rollers and one cylindrical drive member as known in the "mouse-ball" art). Depending on the number of and orientation of roller and drive assemblies used in conjunction with the sphere 3001, it may be understood that the sphere 3001 may be rotated about its center C1 about a number of rotational axes passing through the center C1, including at least three mutually orthogonal axes. In this configuration the Center C1 is approximately in the center of the ankle of the user.

Sphere 3002 is driven by the exemplary roller and drive assembly (which can also include two rollers and one cylindrical drive member as known in the "mouse-ball" art, although these are not shown). Depending on the number of and orientation of roller and drive assemblies used in conjunction with the sphere 3002, it may be understood that the sphere 3002 may be rotated about its center C2 about a number of rotational axes passing through the center C2, including at least three mutually orthogonal axes. In this configuration the Center C2 is distal to the ankle and foot of the user.

It may be understood, therefore, that such a spherical-based configuration could be used to provide at least some of the rotational movements described in association with FIGS. 1-12.

FIG. 14 is an alternate configuration showing the use of a spherical element 3003, except that the center of rotation C3 is even further distal to the foot, and an exemplary calf bias member (aka extender bar) is also used for the AP movement only, with the two other movements being provided without the bias member.

FIG. 15 shows an alternate configuration including a spherical cage 4000 comprised of a plurality of cage bars 4005. Rotation of the cage is done by use of one or more stationary motors such as 4010.

Stationary motor 4010 and rollers 4020 are mounted relative to frame member 4011. Motor 4010 drives rollers 4020, with the two rollers capturing an associated cage bar. This rotation of the spherical cage 4000 can be provided about an axis extending through the center of the cage and normal to a plane including the particular arcuate cage bar. Either of or both rollers can drive the bar. The point of this is to illustrate that many types of drive configurations can be used to provide the motions in certain of the embodiments herein, either from the inside of the sphere, or the outside.

2. Additional RKT Features

Note that the semicircular notch (not numbered) in the pivoting plate 1201 (see for example just under the "Z" axis DRIVE ASSEMBLY 2200 in FIG. 4) is configured to accept a vertical support shaft (not shown) which is anchored at its base and extends upwardly through the plate. The shaft has two slide bearings (not shown) on either side which bear on the two primary planar surfaces of the pivoting plate. This limits up and down deflection of the plate from its pivot point during the AP testing process. During the Y-axis movement, the shaft moves within the slot.

As previously mentioned, it should be understood that any drive configuration could be decoupled from any of the other two—in fact, each of the three drive configurations could be decoupled from each of the other two so that substantially independent rotation about the respective axes thereof may be provided and thus imposed upon the patient's limb, however, as may be desirable for particular applications.

In still other embodiments, it should be understood that two or more, and even all three drive assemblies 2000-2200 may be mutually coupled relative to one another such that movements are substantially simultaneously imposed upon the patient's limb during operation of the overall RKT device. That being said, it is often advantageous to isolate each respective movement; thus isolation (i.e., decoupling) of the movements of each of the respective drive assemblies 2000-2200 may be likewise desirable for particular applications as have been described elsewhere herein.

3. RKT Device for CT Scanning

Additional details regarding imaging protocols, including the use of CT scanning components in conjunction with limb and ligament evaluation apparatuses may be found in Applicant's commonly owned U.S. Patent Application Publication No. 2012/0046540-A1 (also Ser. No. 13/209,380), as published on Feb. 23, 2012 and filed on Aug. 13, 2011, which is hereby incorporated by reference in its entirety.

Further very general disclosure of incorporation of CT scanning components within limb and ligament evaluation apparatuses may be found in Applicant's commonly owned U.S. Patent Application Publication No. 2009/0124936-A1 (also Ser. No. 12/267,109), as published on May 14, 2009 and filed on Nov. 7, 2008, which is hereby incorporated by reference in its entirety.

Here begins a discussion of a second embodiment RKT device 5000, which includes similarities to the above-described RKT device B, but also includes differences. Some of these differences facilitate its use in conjunction with a CT scanner to evaluate the knee of a human. However, it should be understood that this is not to be limited to such scanners or joints, and is only an example. The device 5000 could also be used in conjunction with MRI or other scanners, and indeed some of its features may be used with sensors such as those used with the non-radiographic device 10 above, which include non-invasive systems utilizing sensors or markers that are attached to the skin, including but not limited to optoelectronic, ultrasonic, and electromagnetic motion analysis systems.

Reference is first made to FIG. 17, which is a side illustrative view of a leg testing apparatus 5000 according to one of the inventions herein, in combination with an exemplary CT scanner 4900, and a patient's body support apparatus 4950. The three devices are configured to be typically situated atop an unnumbered supporting surface. Also shown is an exemplary patient, including a patient proper body 4951, patient lower leg 4950, and patient upper leg 4950.

It may be understood that inventions and novelties relate to and include the leg testing apparatus 5000 and its use on its own, as well as the leg testing apparatus 5000 and its use in combination with the CT scanner 4900, as well as the leg testing apparatus 5000 and its use in combination with the patient body support apparatus 4950, as well as the three components 5000, 4950, and 4900 together.

As may be understood, the leg testing apparatus 5000 manipulates the leg of the patient, while the patient is supported on the patient body support apparatus 4950. A portion of the patient's body, in this example the lower leg, is shown in FIG. 17 as within the opening of the CT scanner 4900, such that the lower leg can be scanned by the CT scanner. This scanning may be done while the leg testing apparatus is in any one of a multiplicity of modes of operation, including but not limited to its testing of the patients knee in "AP" (anterior-posterior) movement, varus-valgus movement, and/or internal and external rotation.

The upper torso of the patient is supported by the patient body support apparatus 4950, which includes a back support 4956 (upon which the patient lies), which supports a thigh restraint assembly 4952 (which contains the upper thighs of the patient), and which also supports a shoulder restraint 4959 (which serve to discourage the patient from moving to the right as FIG. 17 is viewed.

It may be understood that under one embodiment of the invention, the patient body support apparatus 4950 includes a structural link member 4951 which connects to the leg testing apparatus 5000, to allow the two to slide together as a unit (with both 5000 being on rollers or suitably aligned tracks). Alternately, the two members could be separately driven via coordinated synchronized drive means.

Reference is now made to FIG. 18, which is a perspective view of a leg testing apparatus 5000 according to one aspect of the present inventions, which includes left lower leg supporting apparatus 5200, right lower leg supporting apparatus 5300, and lower frame number 5100.

As may be seen, in FIG. 18, the "Z" axes of the two apparatuses 5200, and 5300, are not aligned with each other. These two axes are referenced as "Z axis—left", the Z axis of the left apparatus 5200, and "Z axis—right", the Z axis of the right apparatus 5300. The Z axis for purpose of this discussion should be understood as the axis of rotation of the foot plate as discussed in later detail In FIG. 18, these two Z axes are positioned in "alignment" with their related calf bias assemblies 5260, 5360. However it will be understood from later discussion that while the positions of the "Z" axes of the two apparatuses 5200 and 5300 can be varied, the calf bias assemblies are not configured to rotate about a vertical axis (although they can each rotate about their own horizontal "X" axis to provide an AP action). This is to accommodate the use of the apparatus 5000 within the relatively narrow space within the CT scanner.

FIG. 19 is a top elevation view of the leg testing apparatus 5000 of FIG. 18, illustrating the relationship of the left lower leg supporting apparatus 5200 and the right lower leg supporting apparatus 5300, relative to the inner surface of the scanning device 4900. As may be seen, the "X" axes of the two apparatuses 5200, and 5300, are also not aligned, and in the embodiment shown, the angle between the two is fixed.

FIG. 20 is a rear elevation view of the leg testing apparatus 5000 of FIG. 18, which includes left lower leg supporting apparatus 5200, right lower leg supporting apparatus 5300, and lower frame number 5100. FIG. 21 is a front elevation view of the same leg testing apparatus 5000.

FIG. 22 is a pictorial view of the right lower leg supporting apparatus 5300, with certain elements not included for purposes of explanation. In reference to this as well as Figures G and H—for example, here follows a description of right leg supporting apparatus 5300; a similar description could be made of left lower leg supporting apparatus 5200, as the two are essentially mirror images of each other.

The right lower leg supporting apparatus 5300 is slidably mounted relative to the lower frame member via slide assemblies 5101, such that the two apparatuses 5200, 5300, slide in tandem along parallel slide paths. There are smaller slide mounts that allow 5200 and 5300 to slide independently along the same path.

The two slide assemblies 5101 are attached to the bottom of corresponding two lower vertical frame members 5310. A lower frame table 5312 is rigidly attached to the top of the two lower vertical frame members 5310.

Two intermediate vertical frame members 5314 are rigidly attached to the top of the lower frame table 5312. An intermediate frame table 5320 is rigidly attached to the top of the two intermediate vertical frame members 5314.

Two short upper vertical frame members 5322 are rigidly attached to the top of the upper frame table 5312. An upper frame table 5333 is rigidly attached to the top of the two short upper vertical frame members 5322.

Two long upper vertical frame members 5332 are also rigidly attached to the top of the upper frame table 5312. These frame members support the X drive assembly 5600 in a manner similar to that described in the apparatus earlier in this application.

4. "X"-Axis Drive Assembly 5600 Construction and Operation

The "X"-axis Drive Assembly 5600 is configured to drive the calf bias assembly 5360 substantially about the X axis, similar to the manner in which the calf bias assembly 1500 of the device 10 described above was driven by its "X"-axis Drive Assembly 2000. Torque about the X axis is also similarly determined by a similar torque transducer. As in device 10, this provides for an evaluation of "AP" (anterior-posterior) movement of the tibia with respect to the femur at the knee about an X-axis of rotation distal to the foot. It should be understood that such an evaluation, as with any of the movements herein, includes an evaluation of the degree of rotation or pivot as well as the torque involved during such rotation or pivoting.

5. "Y" Drive Assembly Construction and Operation

The "Y" Drive Assembly 5500 is configured to pivot the foot plate 5344 about the horizontal Y axis, such that a foot captured by the foot plate causes varus valgus conditions prompted by forces about a Y-axis of rotation distal to the foot.

The associated Y drive configuration is different than its counterpart in the above device 10. The Y drive assembly 5500 is attached to the underside of lower frame table 5312. It includes an inline reducer and a torque sensor and drives a vertical shaft 5502 which is captured in two bearings, upper and lower bearings 5505 and 5504, respectively. The upper end of the shaft 5502 is rigidly attached to the pivoting horizontal foot support plate 5340 via a flange 5507, such that rotation of the shaft causes rotation of the foot support plate 5340.

A shown in FIG. 25, at the front of the pivoting horizontal foot support plate 5340 is rigidly mounted to a pivoting vertical foot support flange 5341. Flange 5341 supports the Z axis drive assembly 5600, such that operation of the Z axis drive assembly 5600 causes rotation of the foot plate 5344 relative to the flange 5341, about the Z axis. As may be understood, this Z axis can be moved within a horizontal plane, via movement of the "Y" drive assembly.

6. Z Drive Assembly Construction and Operation

As noted above, the Z axis drive assembly 5600 causes rotation of the foot plate 5344 relative to the support flange 5341, about the Z axis. When a foot is contained in the foot plate, this can provide internal and external rotation of the foot and thus the tibia.

7. More Discussion of Decoupling; Different Movements Possible

One drive is "decoupled" from the other if motion by the first drive does not change the position of the second drive in any direction. However, coupling of drive A to drive B does not imply coupling of drive B to drive A. Similarly, decoupling of drive A relative to drive B does not imply decoupling of drive B relative to drive A.

This concept extends to multiple drives such that a system can be configured to have a complex chain of drives working both dependently and/or independently to influence motion of one limb segment with respect to another limb segment. In a global sense, system A of drives could influence the system B of drives but not vice versa.

A first drive is coupled to a second drive if motion of the first drive changes the position of the second drive in any direction. All drives are 'decoupled' when each drive has its own unique independent influence on the position of the tibia with respect to the femur. In the first version described above (leg testing device 10):

The IE Rotation Drive is decoupled from the AP Drive
Both IE Rotation and AP Drives are coupled relative to the Valgus Drive (movement of Valgus Drive affects axis of the other two)

In the second version described above (leg testing device 5000)
AP Drive is totally decoupled
Valgus Drive totally decoupled
IE Rotation Drive is coupled relative to Valgus Drive (movement of Valgus affects axis of IE)
In device 5000, this allows for the following actions:
First place patient limb in extreme internal rotation, then conduct AP test.
First place patient limb in full Valgus as well as full AP, then do anIErotation test
First push patient limb posteriorly, then do varus-valgus test
First put patient limb in extreme varus, then do IErotation test
First place patient limb in extreme varus and extreme rotation, then do AP test 8. Output Data As may be understood, the degrees of the various movements (Varus-Valgus, AP, IE) can be measured by measuring the movements of the machines 10, 5000, themselves, by measuring the degrees of rotation of the drives (by encoding for example) and calibrating as necessary. The torque encountered during each such movement may also be measured, suitably calibrated to the limb movement, and recorded. In the case of the device 10, separate "external" measurement of the limb of the patient may be detected by non-invasive systems utilizes sensors or markers that are attached to the skin, including but not limited to optoelectronic, ultrasonic, and electromagnetic motion analysis systems. In the case of the device 5000, separate measurement of the movement of the limb of the patient may be by using landmarks seen on the actual bones. There are no markers; one can see the bones in the CT images.

9. Testing for Different Degrees of Leg Flexion

It may be understood that during the above tests (AP, varus-valgus, or rotation), there is no flexing of the knee into flexion or extension. However, as shown in FIGS. 26A and 26B, one of the present inventions also includes the additional capability to flex the knee into flexion or extension. This would allow for similar tests (such as the examples above) done for different degrees of knee flex.

10. Variations

Note that instead of the two apparatuses 5200 and 5300 being commonly attached to the lower frame member 5100, they could be each be attached to a separate frame member such that their relative positions on the floor could be independently varied.

The lower frame member 5100 also slides relative to the floor so the whole machine can go in and out

III. CONCLUSION

Many modifications and other embodiments of the invention set forth herein will come to mind to one skilled in the art to which this invention pertains having the benefit of the teachings presented in the foregoing descriptions and the associated drawings.

Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

Although distinct embodiments have been described, the skilled person will understand how features of different embodiments may be combined.

That which is claimed:

1. A limb manipulation and evaluation device comprising:
a frame;
a first drive supported by the frame and configured to manipulate a first bone relative to a second bone in a first direction about a first axis;
a second drive supported by the frame and configured to manipulate said first bone relative to said second bone in a second direction about a second axis; and
a third drive supported by the frame and configured to manipulate said first bone relative to said second bone for movement of the first bone in a third direction,
wherein:
said first, second, and third directions are different directions relative to each other, and
at least one drive of the first, second, and third drives is mutually decoupled relative to another drive of the first, second, and third drives, such that operation of said one drive does not affect position of said another drive relative to the frame, and such that operation of said another drive does not affect position of said one drive.

2. The limb manipulation and evaluation device of claim 1, wherein the first, second, and third directions are orthogonal relative to each other.

3. The limb manipulation and evaluation device of claim 1, wherein the first axis is distal to a foot connected to the first bone.

4. The limb manipulation and evaluation device of claim 1, wherein the first and second drives are distal to a foot connected to the first bone.

5. The limb manipulation and evaluation device of claim 1, wherein the third drive is configured to provide torque about a third axis to move the tibia in the third direction.

6. The limb manipulation and evaluation device of claim 5, wherein the third axis is distal to a foot connected to the first bone.

7. A limb manipulation and evaluation device comprising:
a frame;
a first drive supported by the frame and configured to manipulate a first bone relative to a second bone in a first direction, the first bone being connected to the second bone at a joint;
a second drive supported by the frame and configured to manipulate said first bone relative to said second bone in a second direction; and
a third drive supported by the frame and configured to manipulate said first bone relative to said second bone for movement of the first bone in a third direction,
wherein:
said first, second, and third directions are orthogonal directions relative to each other, and
at least one drive of the first, second, and third drives is mutually decoupled relative to another drive of the first, second, and third drives, such that operation of said one drive does not affect position of said another drive relative to the frame, and such that operation of said another drive does not affect position of said one drive.

8. The limb manipulation and evaluation device of claim 7, wherein the first drive is distal to a foot connected to the first bone.

9. The limb manipulation and evaluation device of claim 7, wherein the first and second drives are distal to a foot connected to the first bone.

10. The limb manipulation and evaluation device of claim 7, wherein the third drive is configured to provide torque about a third axis to move the tibia in the third direction.

11. The limb manipulation and evaluation device of claim 7, wherein the third drive is distal to a foot connected to the first bone.

12. A limb manipulation and evaluation device comprising:
a frame;
a first drive supported by the frame and configured to manipulate tibia relative to a femur in a first direction;
a second drive supported by the frame and configured to manipulate said tibia relative to said femur in a second direction; and
a third drive supported by the frame and configured to manipulate said tibia relative to said femur in a third direction,
wherein:
said first, second, and third directions are different directions relative to each other, and
at least one drive of the first, second, and third drives is mutually decoupled relative to another drive of the first, second, and third drives, such that operation of said one drive does not affect position of said another drive relative to the frame, and such that operation of said another drive does not affect position of said one drive.

13. The limb manipulation and evaluation device of claim 12, wherein the first, second, and third directions are orthogonal relative to each other.

14. The limb manipulation and evaluation device of claim 12, wherein the first drive is distal to a foot connected to the tibia.

15. The limb manipulation and evaluation device of claim 12, wherein the first and second drives are distal to a foot connected to the tibia.

16. The limb manipulation and evaluation device of claim 12, wherein the third direction is anterior-posterior translation.

17. The limb manipulation and evaluation device of claim 16, wherein the third drive is configured to provide torque about an axis to move the tibia in the anterior-posterior direction.

18. The limb manipulation and evaluation device of claim 16, wherein the third drive is distal to a foot connected to the tibia.

19. The limb manipulation and evaluation device of claim 12, wherein the first direction is internal-external rotation of the tibia.

20. The limb manipulation and evaluation device of claim 12, wherein the second direction is varus-valgus rotation of the tibia.

* * * * *